United States Patent
Hamdouchi et al.

(10) Patent No.: US 9,617,263 B2
(45) Date of Patent: Apr. 11, 2017

(54) PHENYL-TRIAZOLO-PYRIDINE COMPOUNDS

(71) Applicant: Eli Lilly and Company, Indianapolis, IN (US)

(72) Inventors: Chafiq Hamdouchi, Carmel, IN (US); Pranab Maiti, West Bengal (IN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/106,998

(22) PCT Filed: Jan. 6, 2015

(86) PCT No.: PCT/US2015/010291
§ 371 (c)(1),
(2) Date: Jun. 21, 2016

(87) PCT Pub. No.: WO2015/105786
PCT Pub. Date: Jul. 16, 2015

(65) Prior Publication Data
US 2017/0029420 A1    Feb. 2, 2017

Related U.S. Application Data

(60) Provisional application No. 61/925,802, filed on Jan. 10, 2014.

(51) Int. Cl.
C07D 471/06   (2006.01)
A61K 31/437   (2006.01)
C07D 471/04   (2006.01)

(52) U.S. Cl.
CPC ................. *C07D 471/04* (2013.01)

(58) Field of Classification Search
CPC ..................... C07D 471/06; A61K 31/437
USPC .......................... 546/119; 514/303
See application file for complete search history.

(56) References Cited

U.S. PATENT DOCUMENTS 9,120,793 B2 *  9/2015  Hamdouchi ......... C07D 471/04

FOREIGN PATENT DOCUMENTS

| EP | 1559422 | 3/2005 |
|---|---|---|
| WO | 2004/041266 | 5/2004 |
| WO | 2005/086661 | 9/2005 |
| WO | 2009/153496 | 12/2009 |
| WO | 2011/161030 | 12/2011 |
| WO | 2013/119040 | 8/2013 |
| WO | 2015/088868 | 6/2015 |
| WO | 2015/105779 | 7/2015 |

* cited by examiner

*Primary Examiner* — Charanjit Aulakh
(74) *Attorney, Agent, or Firm* — MaCharri Vorndran-Jones

(57) ABSTRACT

The present invention provides a compound of the Formula (I) below: wherein $R^1$ is selected from the group consisting of H, $CH_3$, CN, —$CH_2CN$, —$C(CH_3)_2CN$, F, Cl, and Br; $R^2$ is selected from the group consisting of H, —O($C_1$-$C_3$alkylene)R4, —$CH_2CN$, CN, —$OCH_3$, $CF_2$, —$C(CH_3)_2$CN, —$C(CH_3)_2$, —$S(O)_2CH_3$, —$S(O)_2NH_2$, and —$OCF_2$; $R^3$ is selected from the group consisting of H, CH3, and —$OCH_3$; and $R^4$ is selected from the group consisting of H, —$C(CH_3)_2$CN, —$OCH_3$, —$S(O)_2CH_3$, CN, and —$C(CH_3)_2$OH; or a pharmaceutical salt thereof, methods of treating type two diabetes using the compound and a process for preparing the compound.

(I)

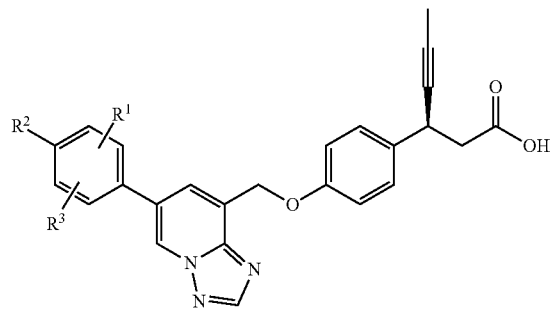

17 Claims, No Drawings

PHENYL-TRIAZOLO-PYRIDINE COMPOUNDS

This invention relates to phenyl-triazolo-pyridine compounds or pharmaceutically acceptable salts thereof and the use for therapy. Phenyl-triazolo-pyridine compounds of this invention are activators of GPR-40.

GPR-40, also known as Free Fatty Acid Receptor 1 (FFA1 or FFAR1), is reported to be predominately expressed at high levels in rodent pancreatic beta cells, insulinoma cell lines, and human islets. The glucose modulation of insulin secretion is an important feature of activating GPR-40. Sulfonylureas, prescribed as insulin secretagogues, are an accepted treatment for patients with type II diabetes; however, additional treatment options are desired. Compounds that effectuate GPR40 activation are associated with stimulation of insulin secretion in a patient with type II diabetes (T2D). Compounds that effectuate GPR40 activation are desired.

WO2004/041266 discloses a compound that is a GPR40 receptor function regulator comprising a compound having an aromatic ring and a group capable of releasing a cation.

There is a need for novel compounds that are GPR 40 activators. The present invention provides compounds with GPR 40 activation activity. Compounds that are GPR 40 activators are desired for use in treatment of GPR 40 mediated conditions.

The present invention provides a compound of the formula:

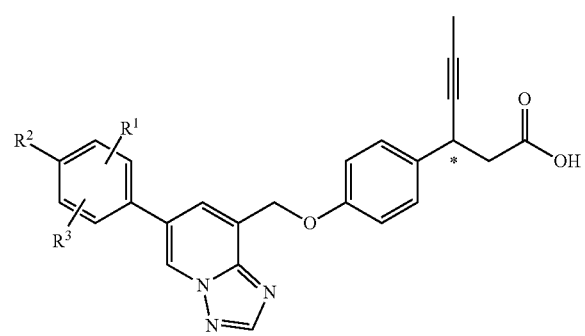

Wherein $R^1$ is selected from the group consisting of H, $CH_3$, CN, $-CH_2CN$, $-C(CH_3)_2CN$, F, Cl, and Br;
$R^2$ is selected from the group consisting of H, $-O(C_1-C_3alkylene)R^4$, $-CH_2CN$, CN, $-OCH_3$, $CF_2$, $-C(CH_3)_2CN$, $-C(CH_3)_2$, $-S(O)_2CH_3$, $-S(O)_2NH_2$, and $-OCF_2$;
$R^3$ is selected from the group consisting of H, $CH_3$, and $-OCH_3$; and
$R^4$ is selected from the group consisting of H, $-C(CH_3)_2CN$, $-OCH_3$, $-S(O)_2CH_3$, CN, and $-C(CH_3)_2OH$;
or a pharmaceutically acceptable salt thereof.

The present invention provides a compound of the Formula I below:

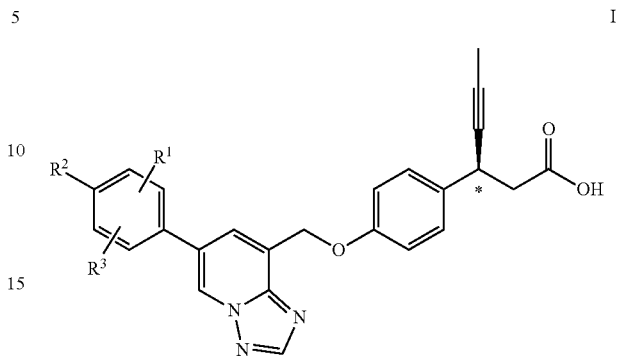

Wherein $R^1$ is selected from the group consisting of H, $CH_3$, CN, $-CH_2CN$, $-C(CH_3)_2CN$, F, Cl, and Br;
$R^2$ is selected from the group consisting of H, $-O(C_1-C_3alkylene)R^4$, $-CH_2CN$, CN, $-OCH_3$, $CF_2$, $-C(CH_3)_2CN$, $-C(CH_3)_2$, $-S(O)_2CH_3$, $-S(O)_2NH_2$, and $-OCF_2$;
$R^3$ is selected from the group consisting of H, $CH_3$, and $-OCH_3$; and
$R^4$ is selected from the group consisting of H, $-C(CH_3)_2CN$, $-OCH_3$, $-S(O)_2CH_3$, CN, and $-C(CH_3)_2OH$;
or a pharmaceutically acceptable salt thereof.

The compounds of the present invention have a chiral carbon identified in the structure above with an asterisk (*). Preferred compounds have the configuration shown above, which by convention is known as the S configuration.

In an embodiment of the present invention $R^1$ is selected from the group consisting of H, $CH_3$, F, and Cl. In another embodiment $R^1$ is selected from the group consisting H and $CH_3$.

In another embodiment of the present invention $R^2$ is selected from the group consisting of H, $-O(C_1-C_3alkylene)R^4$, $-OCH_3$, $-OCF_2$, and $-C(CH_3)_2$. In another embodiment $R^4$ is selected from the group consisting of H, $-S(O)_2CH_3$, $-C(CH_3)_2OH$, and $-OCH_3$. In another embodiment compounds wherein $R^2$ is selected from the group consisting of H, $-O(C_1-C_3alkylene)R^4$, and $C(CH_3)_2$ are preferred.

In another embodiment $R^3$ is selected from the group consisting of H and $CH_3$. In another embodiment, $R^1$ is $CH_3$, $R^2$ is H, and $R^3$ is H.

In another embodiment $R^1$ is selected from the group consisting H and $CH_3$; $R^2$ is selected from the group consisting of H, $-O(C_1-C_3alkylene)R^4$, $-OCH_3$, $-OCF_2$, and $-C(CH_3)_2$; $R^3$ is selected from the group consisting of H and $CH_3$; and $R^4$ is selected from the group consisting of H, $-S(O)_2CH_3$, $-C(CH_3)_2OH$, and $-OCH_3$.

One preferred compound of the present invention is (S)-3-[4-(6-o-Tolyl-[1,2,4]triazolo[1,5-a]pyridin-8-yl-methoxy)-phenyl]-hex-4-ynoic acid; or a pharmaceutically acceptable salt thereof.

The present invention also provides a pharmaceutical composition comprising a compound of Formula I as described above or a pharmaceutically acceptable salt thereof together with one or more pharmaceutically acceptable carriers, diluents or excipients.

The present invention also provides a pharmaceutical composition comprising a compound of Formula I as described above or a pharmaceutically acceptable salt thereof together with one or more pharmaceutically acceptable carriers, diluents or excipients, and optionally one or more therapeutic agents. Additional therapeutic agents include for example, metformin and/or Januvia. In an embodiment the additional therapeutic agent is metformin.

The present invention provides a method for treating a condition modulated by GPR40 activity. The present invention provides a method for treating diabetes in a patient. The method comprises administering to the patient in need of treatment an effective amount compound as described above for Formula I, or a pharmaceutically acceptable salt thereof. More preferably the present invention provides a method of treating type two diabetes in a patient in need of treatment comprising administering a compound as described above for Formula I or a pharmaceutically acceptable salt thereof.

The present invention provides a compound according to Formula I or a pharmaceutically acceptable salt thereof as described above for use in therapy.

In yet another form, the present invention provides a compound as described above according to Formula I, a pharmaceutically acceptable salt thereof, or pharmaceutical composition for use in the treatment of diabetes in a patient in need thereof. Preferably the use is for the treatment of type two diabetes and the patient is a human.

The present invention provides use of a compound according to Formula I, or a pharmaceutically acceptable salt thereof, in the manufacture of a medicament for the treatment of diabetes. Preferably the medicament is for the treatment of type two diabetes.

In yet another form, the present invention provides an intermediate compound of the formula

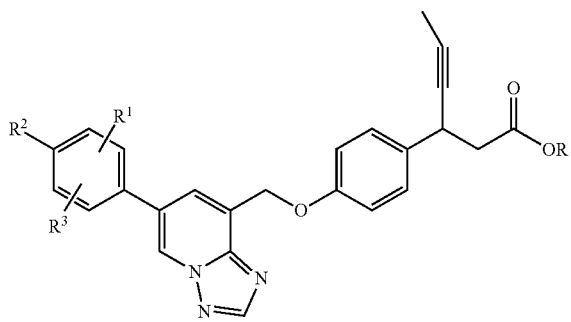

wherein R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl;
$R^1$ is selected from the group consisting of H, $CH_3$, CN, —$CH_2CN$, —$C(CH_3)_2CN$, F, Cl, and Br;
$R^2$ is selected from the group consisting of H, —$O(C_1$-$C_3$alkylene)$R^4$, —$CH_2CN$, CN, —$OCH_3$, $CF_2$, —$C(CH_3)_2$CN, —$C(CH_3)_2$, —$S(O)_2CH_3$, —$S(O)_2NH_2$, and —$OCF_2$;
$R^3$ is selected from the group consisting of H, $CH_3$, and —$OCH_3$; and
$R^4$ is selected from the group consisting of H, —$C(CH_3)_2$CN, —$OCH_3$, —$S(O)_2CH_3$, CN, and —$C(CH_3)_2OH$; to provide a compound of Formula I, or a pharmaceutically acceptable salt thereof. Preferred R groups include $C_{1-2}$ alkyl, $C_{1-2}$ haloalkyl, phenyl, and $C_{1-2}$ alkylphenyl. Particularly preferred R groups include methyl, ethyl, phenyl, and benzyl. It may be preferred that the compound of Formula II, or a salt thereof, comprises a compound wherein $R^1$ is $CH_3$, $R^2$ is H, and $R^3$ is H.

In yet another form, the present invention provides an intermediate compound of the Formula II

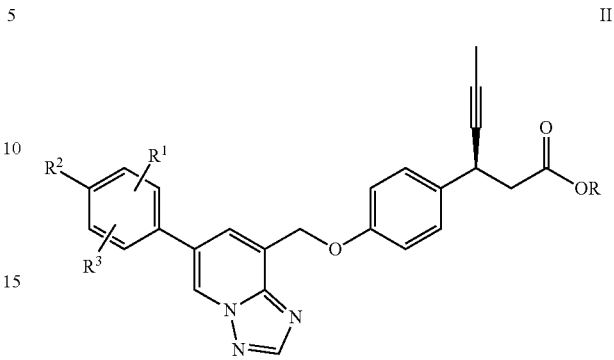

wherein R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl;
$R^1$ is selected from the group consisting of H, $CH_3$, CN, —$CH_2CN$, —$C(CH_3)_2CN$, F, Cl, and Br;
$R^2$ is selected from the group consisting of H, —$O(C_1$-$C_3$alkylene)$R^4$, —$CH_2CN$, CN, —$OCH_3$, $CF_2$, —$C(CH_3)_2$CN, —$C(CH_3)_2$, —$S(O)_2CH_3$, —$S(O)_2NH_2$, and —$OCF_2$;
$R^3$ is selected from the group consisting of H, $CH_3$, and —$OCH_3$; and
$R^4$ is selected from the group consisting of H, —$C(CH_3)_2$CN, —$OCH_3$, —$S(O)_2CH_3$, CN, and —$C(CH_3)_2OH$; to provide a compound of Formula I, or a pharmaceutically acceptable salt thereof. Preferred R groups include $C_{1-2}$ alkyl, $C_{1-2}$ haloalkyl, phenyl, and $C_{1-2}$ alkylphenyl. Particularly preferred R groups include methyl, ethyl, phenyl, and benzyl. It may be preferred that the compound of Formula II, or a salt thereof, comprises a compound wherein $R^1$ is $CH_3$, $R^2$ is H, and $R^3$ is H.

The present invention also provides a process of preparing compounds described above for Formula I. The method comprises deprotecting or de-esterifying the intermediate compound according to Formula II to prepare the compound of Formula 1 or a pharmaceutically acceptable salt thereof.

The invention further provides a compound that selectively activates GPR-40 as compared to PPAR gamma activity, as shown by PPAR gamma functional assay results.

One skilled in the art would readily understand and be able to implement deprotecting reactions without undue experimentation. It will be recognized by those skilled in the art that in addition to the carboxylic acid and protected carboxylic acid, other functional groups that can be readily converted to a carboxylic acid can be used in place of the carboxylic acid or protected acid. Such functional groups, preparations, and transformations of these groups to carboxylic acids can be found in "Comprehensive Organic Transformations: A Guide to Functional Group Preparations" by Larock. R. C, Wiley VCH, 1999 and in "March's Advanced Organic Chemistry, Reactions, Mechanisms and Structure" Smith, M. B., and March, J., Wiley-Interscience, 6th Ed. 2007.

The compounds of the present invention can be provided as pharmaceutically acceptable salts. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

Individual isomers, enantiomers, or diastereomers may be separated at any convenient point in the synthesis of a compound of Formula I by methods such as chiral chromatography. Additionally, the intermediates described in the following Schemes and preparations contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

The abbreviations used herein are defined according to *Aldrichimica Acta*, Vol. 17, No. 1, 1984. Other abbreviations are defined as follows: "BSA" refers to Bovine Serum Albumin; "DIBAL" refers to diisobutylaluminum hydride; "DCM" refers to dichloromethane; "DMEM" refers to Dulbecco's Modified Eagle's Medium; "DMF" refers to dimethylformamide; "DMSO" refers to dimethylsulfoxide; "EC$_{50}$" refers to the effective concentration at half the maximal response; "EtOAc" refers to ethyl acetate; "EtOH" refers to ethyl alcohol or ethanol; "F12" refers to Ham's F12 medium; "FA" refers to fatty acid; "FBS" refers to Fetal Bovine Serum; "HEK" refers to human embryonic kidney; "IC$_{50}$" refers to the concentration of an agent that produces 50% of the maximal inhibitory response possible for that agent; "MeOH" refers to methyl alcohol or methanol; "Pd (amphos)Cl$_2$" refers to bis(di-tert-butyl(4-dimethylaminophenyl)phosphine)dichloropalladium(II); "Pd(PPh$_3$)$_2$Cl$_2$" refers to bis(triphenylphosphine)palladium(II) chloride; "PPA" refers to polyphosphoric acid; "PPAR" refers to peroxisome proliferator-activated receptor; "PPRE" refers to peroxisome proliferator response element; "RFU" refers to relative fluorescence unit; "RPMI" refers to Roswell Park Memorial Institute; "THF" refers to tetrahydrofuran; "TK" refers to thymidine kinase and "TAK875" refers to the Takeda compound known as fasiglifam.

The term alkyl as used herein is a straight chain alkyl such as ethyl or n-propyl, or a branched chain alkyl such as isopropyl or tert-butyl. The term C$_{1-4}$ haloalkyl refers to an alkyl group that has 1, 2, 3, or more halo groups attached to the carbons of the alkyl chain. If there are two or more halogens the halogens need not be attached to the same carbon. This term also includes perhalo alkyls where all the hydrogen atoms of the alkyl group are replaced with a halogen.

In the Schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

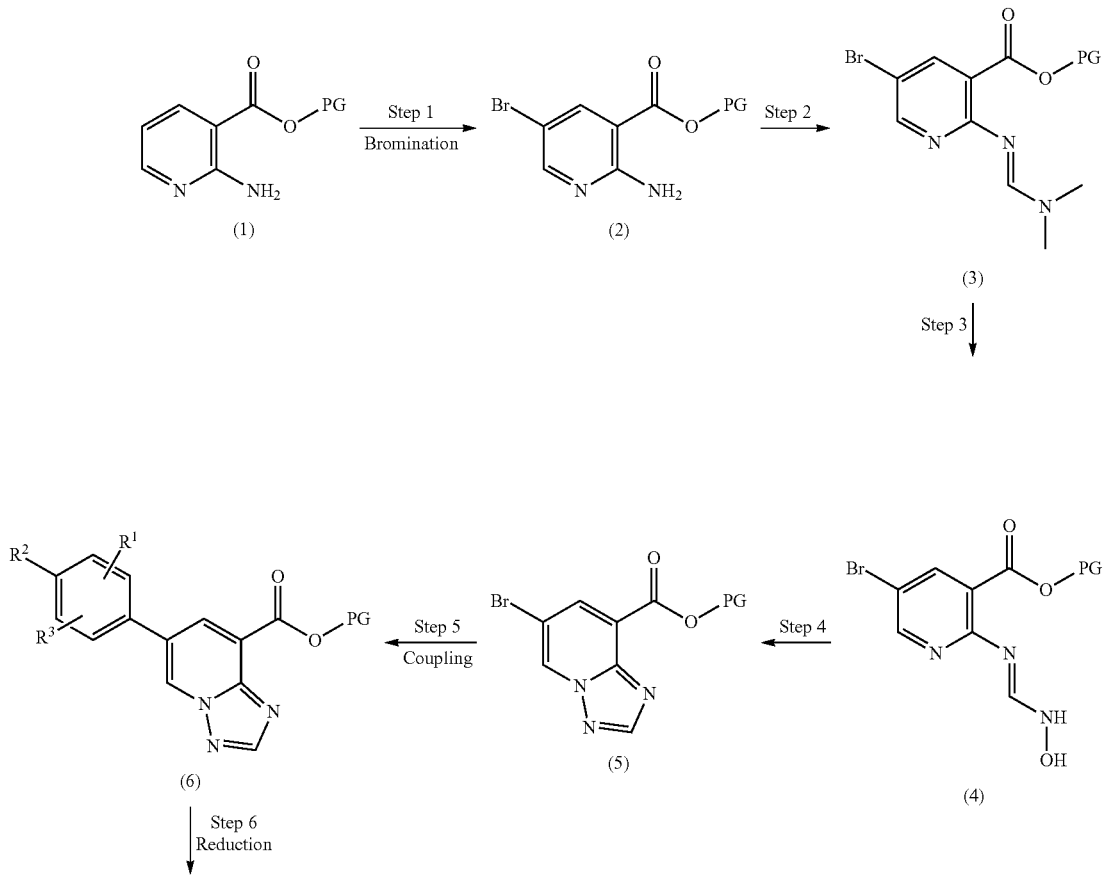

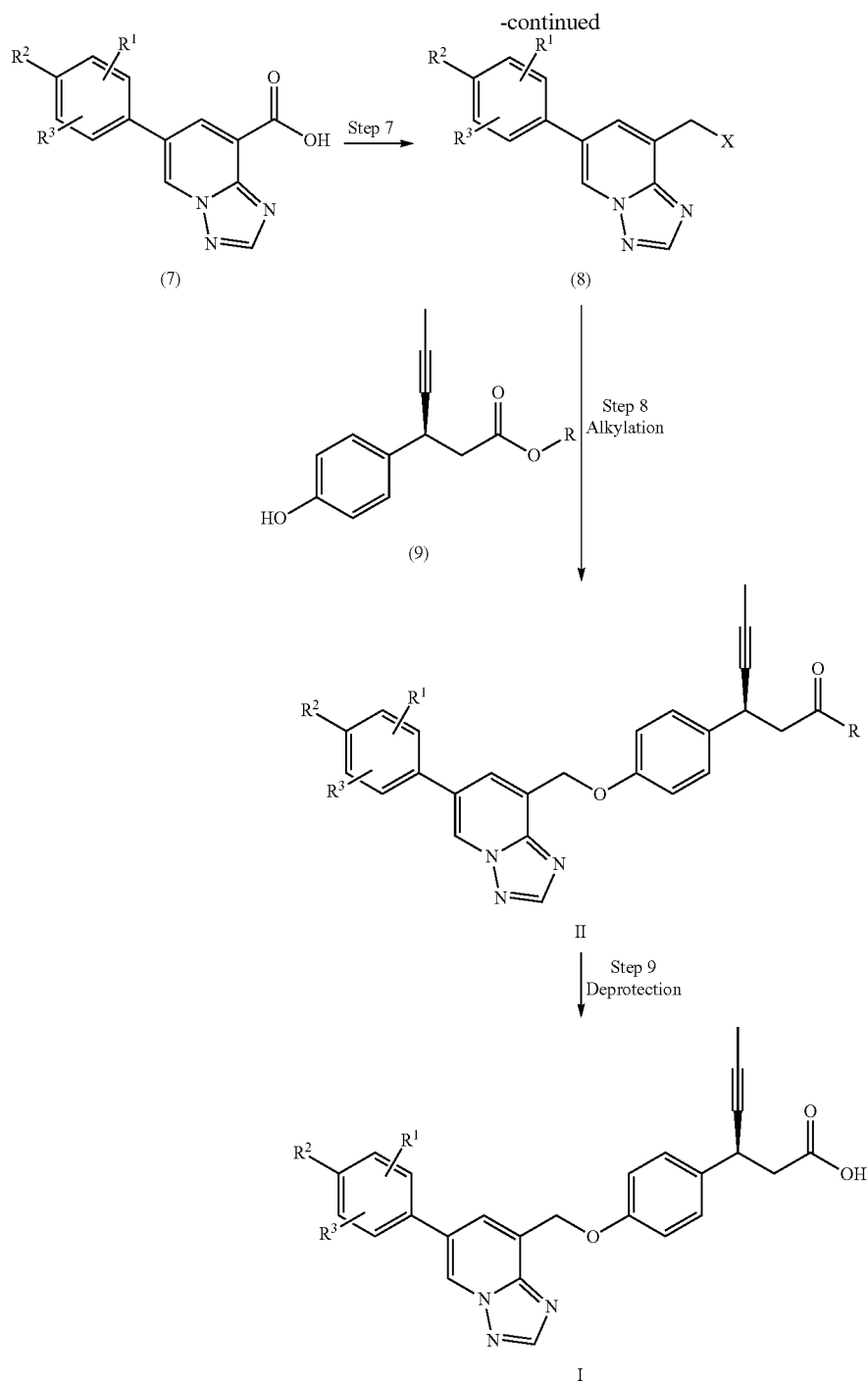

PG = protecting group
X = Br or Cl

A compound of Formula I can be prepared in accordance with reactions as depicted in Scheme 1. A 2-amino-3-carboxy ester pyridine is brominated exclusively at the most activated 5 position using bromine and an inorganic base such as sodium bicarbonate in a polar aprotic solvent such as DCM to give compound 2, Step 1. In Step 2, the primary amine at the 2 position of the pyridine is converted to the dimethylamino-methyleneamino compound (3) by a formamide condensation using dimethoxy methyl dimethylamine in a polar aprotic solvent such as DMF to give compound 3, Step 2. Compound 3 is converted to the hydroxyl amine imine (4) using hydroxylamine hydrochloride in a polar protic solvent such as MeOH to give compound 4, Step 3. Compound 4 can be cyclized to the [1,2,4]triazolo[1,5-a]pyridine (5) by an acid catalyzed intramolecular cyclization to give the tetrazole (5) with polyphosphoric acid and heating to about 120° C., Step 4. Alternatively, the [1,2,4]triazolo[1,5-a]pyridine (5) can be formed using trifluoroacetic anhydride in a polar aprotic solvent such as THF at about 0° C. to give compound 5. The 8-bromo [1,2,4]

triazolo[1,5-a]pyridine (5, Step 5) can be coupled under Suzuki-Miyaura cross coupling conditions using a boronic acid reagent. The skilled artisan will recognize that there are a variety of conditions useful for facilitating such cross coupling reactions. Accordingly, a suitable palladium reagent includes bis(triphenylphosphine)palladium(II) dichloride, Pd(amphos)Cl$_2$, tris(dibenzylideneacetone)dipalladium (0) with tricyclohexylphosphine, (1,1'-bis(diphenylphosphino)ferrocene)palladium (II) chloride, palladium tetrakistriphenylphosphine, or palladium(II) acetate. A suitable base includes cesium carbonate, sodium carbonate, potassium carbonate, or potassium phosphate tribasic monohydrate in a suitable non-polar solvent such as 1,4-dioxane to give compound 6, Step 5. The ester of compound 6 can be reduced to the hydroxy compound (7, Step 6) with diisobutylaluminum hydride (DIBAL) in a polar aprotic solvent such as dichloromethane or THF to give compound 7, Step 6. The hydroxy compound can be converted to either the chloride or bromide in Step 7, compound 8. A typical chlorinating agent is thionyl chloride while typical brominating agents are phosphorus tribromide or carbon tetrabromide and triphenylphosphine in a polar aprotic solvent such as DCM to give compound 8, Step 7 where X is Cl or Br. The halogenated compound (8) can then be alkylated with compound 9 under basic conditions using an inorganic base such as cesium carbonate or potassium acetate in a polar aprotic solvent such as acetonitrile to give the ester protected compounds of Formula II, Step 8. The protected acid from Step 8 can be deprotected under basic conditions well known in the art to give compounds of Formula I, Step 9. Conditions for deprotection of esters are well known in the art using a base such as sodium hydroxide or lithium hydroxide in a polar protic solvent such as EtOH or MeOH or a water/THF solvent mixture. Other alternative deprotection conditions include using trimethyltin hydroxide or potassium trimethylsilanolate as a base in dichloroethane or THF to give compounds of Formula I.

The following preparations and examples further illustrate the invention and represent typical synthesis of the compounds of Formula I. Unless noted to the contrary, the compounds illustrated herein are named and numbered using Accelrys Draw 4.0, IUPCNAME ACDLABS or MDL ISIS, version 2.5 SP2.

Preparation 1

2-Amino-5-bromo-nicotinic acid ethyl ester

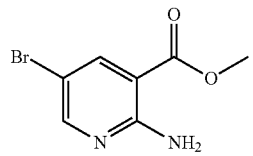

To a stirred solution of 2-amino-nicotinic acid methyl ester (2 g, 13.15 mmol) and sodium bicarbonate (2.2 g, 26.31 mmol) in DCM (30 mL) is added a solution of bromine (1.01 mL in DCM (20 mL) drop wise at 0° C. The reaction mixture is stirred at room temperature for 1 hour. The reaction mixture is quenched with sodium bisulfite solution (50 mL) and extracted with DCM (2×40 mL). The combined organic layers are washed with brine (40 mL), dried over sodium sulphate, filtered, and evaporated under reduced pressure to give the title compound as a yellow solid (3 g, 99%). LCMS m/z ($^{79}$Br/$^{81}$Br) 231/233 (M+H)$^+$.

Preparation 2

5-Bromo-2-(dimethylamino-methyleneamino)-nicotinic acid methyl ester

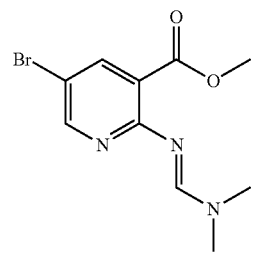 [SMILES: COC(=O)c1cc(Br)cnc1/N=C/N(C)C]

To a solution of 2-amino-5-bromo-nicotinic acid ethyl ester (3 g, 12.98 mmol) in DMF (30 mL) is added dimethoxymethyl dimethylamine (5.1 mL, 38.95 mmol) at room temperature. The reaction mixture is heated at 110° C. for overnight. The reaction mixture is diluted with ice water (50 mL) and extracted with EtOAc (2×40 mL). The combined organic layers are washed with brine (40 mL), dried over sodium sulphate, filtered, and evaporated under reduced pressure to give the title compound (3.2 g, 86%) which is used without further purification. LCMS m/z ($^{79}$Br/$^{81}$Br) 286/288 (M+H)$^+$.

Preparation 3

5-Bromo-2-[(N-hydroxy-formimidoyl)-amino]-nicotinic acid methyl ester

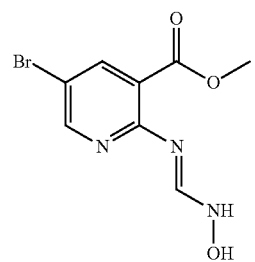

To a solution of 5-bromo-2-(dimethylamino-methyleneamino)-nicotinic acid methyl ester (3.2 g, 11.10 mmol) in MeOH (30 mL) is added hydroxylamine hydrochloride (1.0 g, 15.54 mmol) at 0° C. The reaction mixture is stirred at room temperature for 1 hour. The reaction mixture is evaporated under reduced pressure and the residue is washed with water (10 mL), filtered, and dried to give the title compound (3 g, 100%) which is used without further purification. LCMS m/z ($^{79}$Br/$^{81}$Br) 274/276 (M+H)$^+$.

Preparation 4

6-Bromo-[1,2,4]triazolo[1,5-a]pyridine-8-carboxylic acid methyl ester

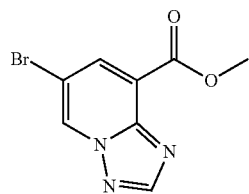

5-Bromo-2-[(N-hydroxy-formimidoyl)-amino]-nicotinic acid methyl ester (3 g, 10.86 mmol) is added in portions to PPA (0.8 g) at room temperature. Then the reaction mixture is heated at 120° C. overnight. The reaction mixture is quenched with sodium bicarbonate solution (50 mL) and extracted with EtOAc (2×40 mL). The combined organic extracts are washed with brine (40 mL), dried over sodium sulphate, filtered, and evaporated under reduced pressure. The residue is purified by silica gel column chromatography (combiflash), eluting with 40% EtOAc in hexanes to give the title compound as an off white solid (0.6 g, 21.42%). LCMS m/z ($^{79}$Br/$^{81}$Br) 256/258 (M+H)$^+$.

Alternate Preparation 4

To a stirred solution of 5-bromo-2-[(N-hydroxy-formimidoyl)-amino]-nicotinic acid methyl ester (14 g, 51 mmol) in THF (100 mL) is added trifluoroacetic anhydride (10.8 mL, 76 mmol) at 0° C. The reaction mixture is stirred at room temperature overnight. The reaction mixture is then quenched with sodium bicarbonate solution (250 mL) and extracted with EtOAc (2×250 mL). The combined organic extracts are washed with brine (100 mL), dried over sodium sulphate, filtered, and evaporated under reduced pressure. The residue is purified by silica gel column chromatography (combiflash) eluting with 30% EtOAc in hexanes to give the title compound as an off white solid (6.5 g, 50%). LCMS m/z ($^{79}$Br/$^{81}$Br) 256/258 (M+H)$^+$.

Preparation 5

2-(5-Chloro-2-methyl-phenyl)-4,4,5,5-tetramethyl-[1,3,2]dioxaborolane

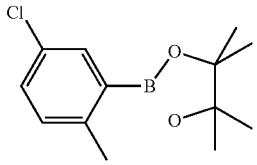

To a stirred solution of 5-chloro-2-methyl-phenylamine (1.5 g 10.59 mmol) in acetonitrile (30 mL) is added tert-butylnitrite (1.88 mL, 15.88 mmol) and bispinacolato diboron (4.03 g, 15.89 mmol) at 0° C. The mixture is heated at 80° C. for 2 hours. The reaction mixture is evaporated under reduced pressure to obtain crude compound which is purified by silica gel column chromatography (combiflash) eluting with 4% ethyl acetate/hexanes to give the title compound (1 g, 38%). LCMS m/z 253 (M+H)$^+$.

Preparation 6

4-Isopropyl-phenylboronic acid

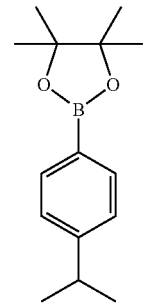

To a stirred solution of 4-isopropyl-phenylamine (1 g, 7.4 mmol) in acetonitrile (30 mL) is added tert-butylnitrite (1.3 mL, 11.1 mmol) and bispinacolatodiboron (2.24 g, 8.8 mmol) at 0° C. The mixture is heated at 80° C. for 2 hours. The reaction mixture is evaporated under reduced pressure and purified by silica gel column chromatography (combiflash) eluting in 4% EtOAc/hexanes to give the title compound as a brown solid (1.2 g, 99.8%). $^1$HNMR (400 MHz, CDCl$_3$) δ 7.74 (d, J=8.0 Hz, 2H), 7.24 (d, J=8.4 Hz, 2H), 2.93-2.87 (m, 1H), 1.33 (s, 12H), 1.25 (d, J=7.2 Hz, 6H).

Preparation 7

4-Bromo-2-methyl-butan-2-ol

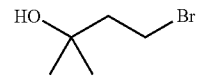

To a stirred solution of 4-bromo-butyric acid methyl ester (1 g, 5.9 mmol) in diethyl ether (20 mL) is added methyl magnesium bromide (19.9 mL, 23.9 mmol) at 0° C. and the mixture is stirred at room temperature for 1 hour. The reaction mixture is quenched with aqueous ammonium chloride (40 mL) and extracted with diethyl ether (2×20 mL). The combined organic extracts are washed with saturated brine solution (20 mL), dried over sodium sulphate, filtered, and concentrated. The crude material is purified by silica gel column chromatography (combiflash) eluting with 20% EtOAc/hexanes to obtain title compound as pale pink liquid (0.6 g, 60%). $^1$HNMR (400 MHz, DMSO) δ 4.38 (s, 1H), 3.52-3.48 (m, 2H), 1.97-1.91 (m, 2H), 1.08 (s, 6H).

Preparation 8

6-o-Tolyl-[1,2,4]triazolo[1,5-a]pyridine-8-carboxylic acid methyl ester

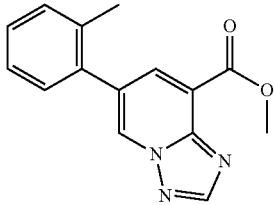 [SMILES: COC(=O)c1cc(-c2ccccc2C)cn2ncnc12]

To a stirred solution of 6-bromo-[1,2,4]triazolo[1,5-a]pyridine-8-carboxylic acid methyl ester (0.2 g, 0.78 mmol) and o-tolyl boronic acid (0.11 g, 0.859 mmol) in dioxane (4 mL) is added a solution of 2 M potassium carbonate (0.78 mL, 1.56 mmol) at room temperature. The reaction mixture is purged with argon for 30 minutes and Pd(PPh$_3$)$_4$ (0.045 g, 0.039 mmol) is added. Then the reaction mixture is heated at 100° C. for 1 hour in a microwave. After completion of the reaction, the reaction mixture is passed through diatomaceous earth, the filtrate is diluted with water (20 mL) and extracted with EtOAc (2×30 mL). The combined organic extracts are washed with water (20 mL), brine (20 mL), dried over sodium sulphate, filtered, and evaporated under reduced pressure. The residue is purified by silica gel column chromatography (combiflash) eluting with 40% EtOAc in hexanes to give the title compound (0.11 g, 52.88%). LCMS m/z 268.1 (M+H)$^+$.

Alternate Preparation 8

To a stirred solution of 6-bromo-[1,2,4]triazolo[1,5-a]pyridine-8-carboxylic acid methyl ester (432 g, 1.69 mol) and o-tolyl boronic acid (252.3 g, 1.855 mol) in toluene (8.6 L) is added a solution of K$_3$PO$_4$ (1074 g, 5.05 mol) in water (5 L). The reaction mixture is purged with nitrogen for 1 hour, Pd(amphos)Cl$_2$ (29.87 g, 0.0421 mol) is added and the mixture is purged again with nitrogen for 20 minutes. The reaction mixture is heated at 70° C. for 2 hours. The reaction is cooled to 30° C., filtered through diatomaceous earth, and washed with EtOAc (3×1 L). The filtrate is diluted with water (5 L) and the aqueous layer is extracted with EtOAc (2×2 L). The combined organic extracts are washed with water (3 L) and saturated brine solution (3 L), dried over sodium sulfate, filtered, and concentrated to dryness. This crude material (273 g) is mixed with crude material of other lots (330 g batch size and 432 g batch size) and purified with silica gel column chromatography eluting with 60-70% EtOAc/hexanes to obtain the title compound as an off white solid (354 g, 28.4%). LCMS m/z 268.1 (M+H)$^+$.

The following compound is prepared essentially by the method of Preparation 8.

TABLE 1

| Prep. No | Chemical Name | Structure | ES/MS (m/z) (M + 1) |
|---|---|---|---|
| 9 | 6-(2-Fluoro-5-methoxyphenyl)-[1,2,4]triazolo[1,5-a]pyridine-8-carboxylic acid methyl ester | 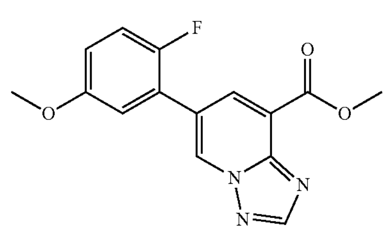 | 302 |

Preparation 10

6-(4-Methoxy-2, 6-dimethyl-phenyl)-[1, 2, 4]triazolo [1, 5-a]pyridine-8-carboxylic acid methyl ester

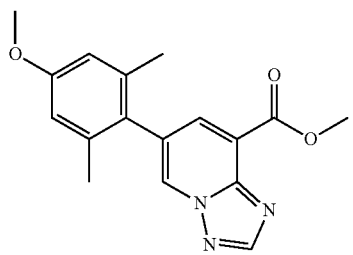 [SMILES: COC(=O)c1cc(-c2c(C)cc(OC)cc2C)cn2ncnc12]

To a stirred solution of 6-bromo-[1,2,4]triazolo[1,5-a]pyridine-8-carboxylic acid methyl ester (0.8 g, 3.125 mmol) and 2,5 dimethyl 4-methoxy phenyl boronic acid (0.563 g, 0.315 mmol) in 1,4 dioxane (12 mL) is added potassium carbonate (1.29 g, 9.38 mmol) and the reaction is purged under a nitrogen atmosphere for 20 minutes. To this solution is added Pd(PPh$_3$)$_4$ (0.18 g, 0.156 mmol) and the reaction mixture is heated at 100° C. in a microwave for 8 hours. The reaction mixture is diluted with EtOAc (30 mL) and washed with water (2×30 mL) and brine solution (30 mL), dried over anhydrous sodium sulphate filtered, and evaporated under reduced pressure. The residue is purified by silica gel column chromatography (combiflash) eluting at 29-32% EtOAc in hexanes to give the title compound as a yellow solid (0.375 g, 38%). LCMS m/z 312 (M+H)$^+$.

Preparation 11

6-(4-Methoxy-phenyl)-[1,2,4]triazolo[1,5-a]pyridine-8-carboxylic acid methyl ester

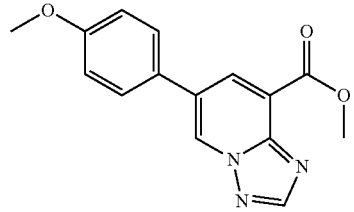

To a stirred solution of 6-bromo-[1,2,4]triazolo[1,5-a]pyridine-8-carboxylic acid methyl ester (0.5 g, 1.95 mmol) and 4-methoxyphenyl boronic acid (0.32 g, 2.1 mmol) in dioxane (20 mL) is added a solution of 2 M potassium carbonate (0.8 g, 5.8 mmol) at room temperature. The reaction mixture is purged with argon for 30 minutes and Pd(PPh$_3$)$_2$Cl$_2$ (0.068 g, 0.096 mmol) is added. The reaction mixture is heated at 100° C. for 2 hours. The reaction mixture is passed through diatomaceous earth and the filtrate is evaporated to dryness under reduced pressure. The crude is used without further purification (0.52 g, 94%). LCMS m/z 284 (M+H)$^+$.

The following compounds are prepared essentially by the method of preparation 11.

TABLE 2

| Prep. No | Chemical Name | Structure | ES/MS (m/z) (M + 1) |
|---|---|---|---|
| 12 | 6-(4-Methanesulfonyl-phenyl)-[1,2,4]triazolo[1,5-a]pyridine-8-carboxylic acid methyl ester | 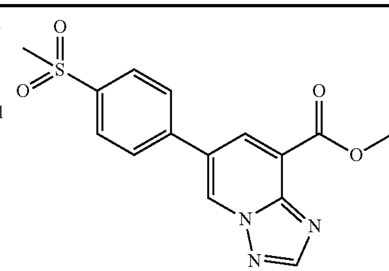 | 331 |
| 13 | 6-(4-Formyl-phenyl)-[1,2,4]triazolo[1,5-a]pyridine-8-carboxylic acid methyl ester | 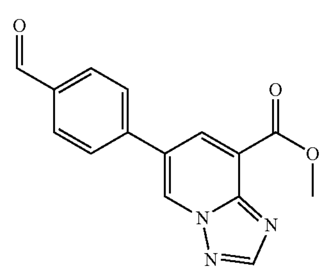 [SMILES: COC(=O)c1cc(-c2ccc(C=O)cc2)cn2ncnc12] | 282 |

Preparation 14

6-(2,6-Dimethyl-phenyl)-[1,2,4]triazolo[1,5-a]pyridine-8-carboxylic acid methyl ester

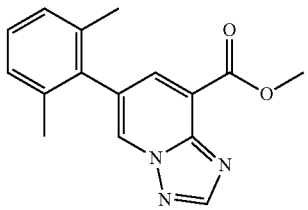 [SMILES: COC(=O)c1cc(-c2c(C)cccc2C)cn2ncnc12]

To a stirred solution of 6-bromo-[1,2,4]triazolo[1,5-a]pyridine-8-carboxylic acid methyl ester (2 g, 738 mmol) and 2,3-dimethyl phenyl boronic ester (1.7 g, 11.7 mmol) in dioxane (20 mL) is added $K_2CO_3$ (2.1 g, 15.6 mmol). The mixture is purged with argon for 30 minutes. To this is added $Pd(PPh_3)_2Cl_2$ (0.273 g, 0.39 mmol) and the mixture is heated at 100° C. for overnight. The reaction mixture is cooled to room temperature and filtered through diatomaceous earth. The filtrate is diluted with water (30 mL) and extracted with EtOAc (2×30 mL). The combined organic extracts are washed with saturated brine solution (20 mL), dried over sodium sulphate, filtered, and concentrated. The crude material is purified by silica gel column chromatography (combiflash) eluting with 30% EtOAc/hexanes to give the title compound as a colorless liquid (0.7 g, 33.3%). LCMS m/z 282 $(M+H)^+$.

Preparation 15

(6-o-Tolyl-[1,2,4]triazolo[1,5-a]pyridin-8-yl)-methanol

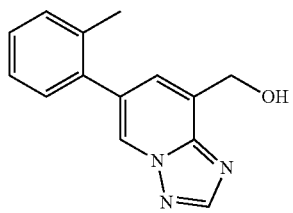 [SMILES: Cc1ccccc1-c1cc(CO)c2ncnn2c1]

To a stirred solution of 6-o-tolyl-[1,2,4]triazolo[1,5-a]pyridine-8-carboxylic acid methyl ester (0.11 g, 0.411 mmol) in DCM (10 mL) is added DIBAL (1.12 mL, 1.1 M in hexanes, 1.87 mmol) at −78° C. The reaction mixture is allowed to warm to room temperature and stirred for 2 hours. The reaction mixture is quenched with MeOH (4 mL) at 0° C. and stirred for 30 min at room temperature. The reaction mixture is passed through diatomaceous earth and the filtrate is concentrated under reduced pressure to give the title compound (0.09 g, crude) which is used without further purification. LCMS m/z 240.2 $(M+H)^+$.

The following compounds are prepared essentially by the method of preparation 15.

TABLE 3

| Prep. No | Chemical Name | Structure | ES/MS (m/z) (M + 1) |
|---|---|---|---|
| 16 | [6-(4-Methoxy-phenyl)-[1,2,4]triazolo[1,5-a]pyridin-8-yl]-methanol | 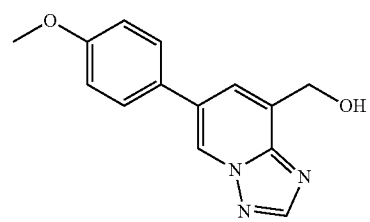 [SMILES: COc1ccc(-c2cc(CO)c3ncnn3c2)cc1] | 256 |
| 17 | [6-(4-Methoxy-2,6-dimethyl-phenyl)-[1,2,4]triazolo[1,5-a]pyridin-8-yl]-methanol | 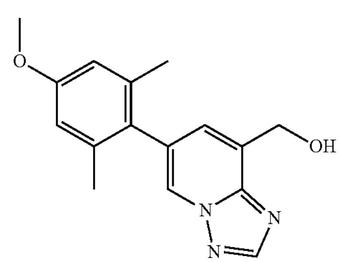 [SMILES: COc1cc(C)c(-c2cc(CO)c3ncnn3c2)c(C)c1] | 284 |

TABLE 3-continued

| Prep. No | Chemical Name | Structure | ES/MS (m/z) (M + 1) |
|---|---|---|---|
| 18 | [6-(4-Dimethoxymethyl-phenyl)-[1,2,4]triazolo[1,5-a]pyridin-8-yl]-methanol | 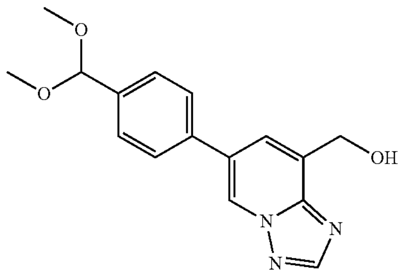 [SMILES: COC(OC)c1ccc(-c2cc(CO)c3ncnn3c2)cc1] | 300 |
| 19 | [6-(2,6-Dimethylphenyl)[1,2,4]-triazolo[1,5-a]pyridin-8-yl]methanol | 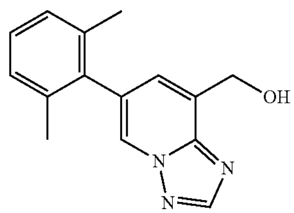 [SMILES: Cc1cccc(C)c1-c1cc(CO)c2ncnn2c1] | 253 |
| 20 | (6-Bromo-[1,2,4]triazolo[1,5-a]pyridin-8-yl)-methanol | 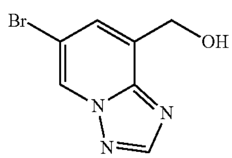 [SMILES: OCc1cc(Br)cn2ncnc12] | 229 |

Preparation 21

[6-(2-Fluoro-5-methoxy-phenyl)-[1,2,4]triazolo[1,5-a]pyridin-8-yl]-methanol

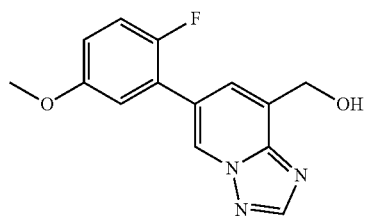 [SMILES: COc1ccc(F)c(-c2cc(CO)c3ncnn3c2)c1]

To a stirred solution of 6-(2-fluoro-5-methoxy-phenyl)-[1,2,4]triazolo[1,5-a]pyridine-8-carboxylic acid methyl ester (0.4 g, 1.33 mmol) in THF (15 mL) is added DIBAL (6.6 mL, 1 M in hexane, 6.6 mmol) at −78° C. The reaction mixture is allowed to warm to room temperature and stirred overnight. The reaction mixture is quenched with ammonium chloride (10 mL) at 0° C. and extracted with EtOAc (3×15 mL). The combined organic extracts are dried over sodium sulphate, filtered, and evaporated under reduced pressure to give the title compound (0.38 g, 100%). LCMS m/z 274 (M+H)$^+$.

The following compound is prepared essentially by the method of preparation 21.

TABLE 4

| Prep. No | Chemical Name | Structure | ES/MS (m/z) (M + 1) |
|---|---|---|---|
| 22 | [6-(4-Methanesulfonyl-phenyl)-[1,2,4]triazolo[1,5-a]pyridin-8-yl]-methanol | 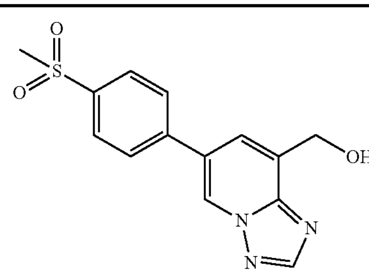 | 304 |

Preparation 23

8-Chloromethyl-6-o-tolyl-[1,2,4]triazolo[1,5-a]pyridine

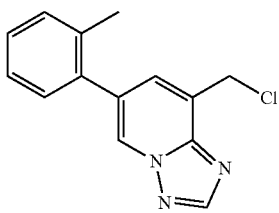 [SMILES: Cc1ccccc1-c1cc(CCl)c2ncnn2c1]

(6-o-Tolyl-[1,2,4]triazolo[1,5-a]pyridin-8-yl)-methanol (0.09 g, 0.37 mmol) is dissolved in thionyl chloride (5 mL) and the reaction mixture is stirred for 1 hour at room temperature. The reaction mixture is partitioned between water (20 mL) and DCM (50 mL). The organic layer is washed with $NaHCO_3$ solution (25 mL), dried over sodium sulphate, and evaporated under reduced pressure to give the title compound (0.07 g, crude). LCMS m/z 258.1 $(M+H)^+$.

The following compounds are prepared essentially by the method of preparation 23.

TABLE 5

| Prep. No | Chemical Name | Structure | ES/MS (m/z) (M + 1) |
|---|---|---|---|
| 24 | 8-Chloromethyl-6-(4-methoxy-phenyl)-[1,2,4]triazolo[1,5-a]pyridine | 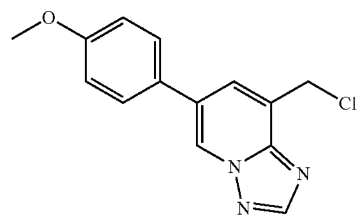 [SMILES: COc1ccc(-c2cc(CCl)c3ncnn3c2)cc1] | 274 |
| 25 | 8-Chloromethyl-6-(2,6-dimethyl-phenyl)-[1,2,4]triazolo[1,5-a]pyridine | 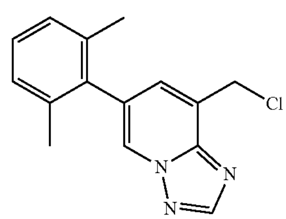 [SMILES: Cc1cccc(C)c1-c1cc(CCl)c2ncnn2c1] | 272 |
| 26 | 6-Bromo-8-chloromethyl-[1,2,4]triazolo[1,5-a]pyridine | 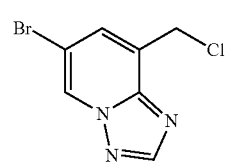 [SMILES: ClCc1cc(Br)cn2ncnc12] | 246/248 |

Preparation of 27

8-(Bromomethyl)-6-(4-methoxy-2,6-dimethylphenyl)[1,2,4]triazolo[1,5-a]pyridine

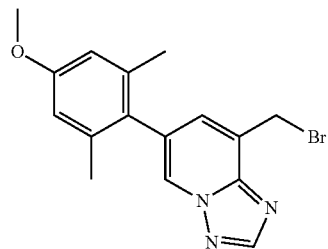 [SMILES: COc1cc(C)c(-c2cc(CBr)c3ncnn3c2)c(C)c1]

To a solution of [6-(4-methoxy-2,6-dimethyl-phenyl)-[1,2,4]triazolo[1,5-a]pyridin-8-yl]-methanol (0.200 g, 0.704 mmol) in DCM (6 mL) is added PBr$_3$ (0.1 mL, 0.84 mmol) at 0° C. The mixture is allowed to stir at room temperature for 1 hour. The reaction mixture is cooled to 0° C., quenched with saturated sodium bicarbonate solution (20 mL) and extracted with DCM (3×20 mL). The combined organic extracts are washed with brine solution (15 mL), dried over sodium sulphate, filtered, and evaporated to dryness to give the title compound (0.250 g, crude). LCMS m/z ($^{79}$Br/$^{81}$Br) 346/348 (M+H)$^+$ The following compounds are prepared essentially by the method of preparation 27.

Preparation 30

(S)-3-[4-(6-o-tolyl-[1,2,4]Triazolo[1,5-a]pyridin-8-ylmethoxy)-phenyl]-hex-4-ynoic acid ethyl ester

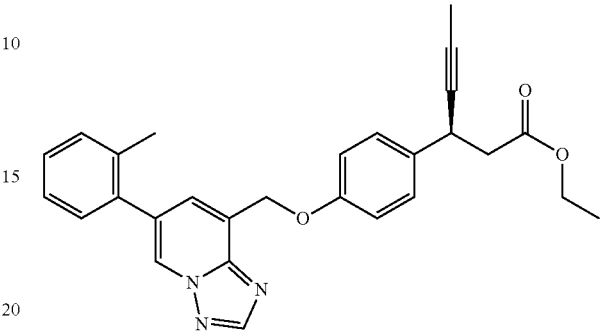

To a stirred solution of 8-chloromethyl-6-o-tolyl-[1,2,4]triazolo[1,5-a]pyridine (0.07 g, 0.27 mmol) and (S)-3-(4-hydroxy-phenyl)-hex-4-ynoic acid ethyl ester (WO05/086661) (0.06 g, 0.27 mmol) in acetonitrile (10 mL) is added cesium carbonate (0.409 g, 1.25 mmol) at room temperature. The reaction mixture is stirred at room temperature overnight. The reaction mixture is filtered and evaporated under reduced pressure. The residue is diluted with EtOAc (15

TABLE 6

| Prep. No | Chemical Name | Structure | ES/MS (m/z) (M + 1) |
|---|---|---|---|
| 28 | 8-Bromomethyl-6-(2-fluoro-5-methoxy-phenyl)-[1,2,4]triazolo[1,5-a]pyridine | 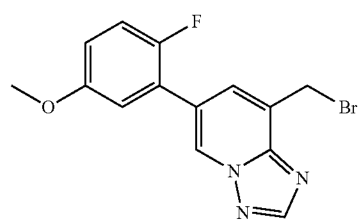 [SMILES: COc1ccc(F)c(-c2cc(CBr)c3ncnn3c2)c1] | 336/338 |
| 29 | 8-Bromomethyl-6-(4-methanesulfonyl-phenyl)-[1,2,4]triazolo[1,5-a]pyridine | | 366/368 | mL), the organic layer is washed with water (20 mL), brine (20 mL), dried over sodium sulphate, filtered, and evaporated under reduced pressure. The residue is purified by silica gel column chromatography (combiflash) eluting with 35% EtOAc in hexanes to give the title compound (0.08 g, 80.34%). LCMS m/z 454.3 (M+H)+.

The following compounds are prepared essentially by the method of preparation 30.

TABLE 7

| Prep. No | Chemical Name | Structure | ES/MS (m/z) (M + 1) |
|---|---|---|---|
| 31 | (S)-3-{4-[6-(4-Methoxy-phenyl)-[1,2,4]triazolo[1,5-a]pyridin-8-ylmethoxy]-phenyl}-hex-4-ynoic acid ethyl ester | 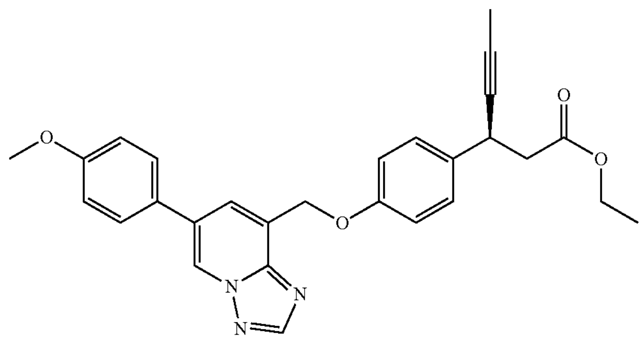 [SMILES: CC#C[C@@H](CC(=O)OCC)c1ccc(OCc2cc(-c3ccc(OC)cc3)cn3ncnc23)cc1] | 470 |
| 32 | (S)-3-{4-[6-(4-Methoxy-2,6-dimethyl-phenyl)-[1,2,4]triazolo[1,5-a]pyridin-8-ylmethoxy]-phenyl}-hex-4-ynoic acid ethyl ester | 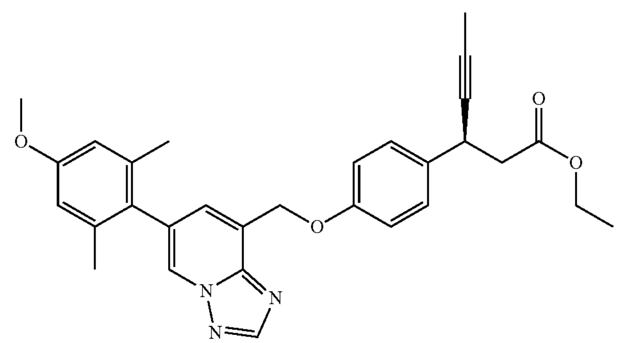 [SMILES: CC#C[C@@H](CC(=O)OCC)c1ccc(OCc2cc(-c3c(C)cc(OC)cc3C)cn3ncnc23)cc1] | 498 |
| 33 | 3-{4-[6-(5-Methoxy-2-methyl-phenyl)-[1,2,4]triazolo[1,5-a]pyridin-8-ylmethoxy]-phenyl}-hex-4-ynoic acid ethyl ester | 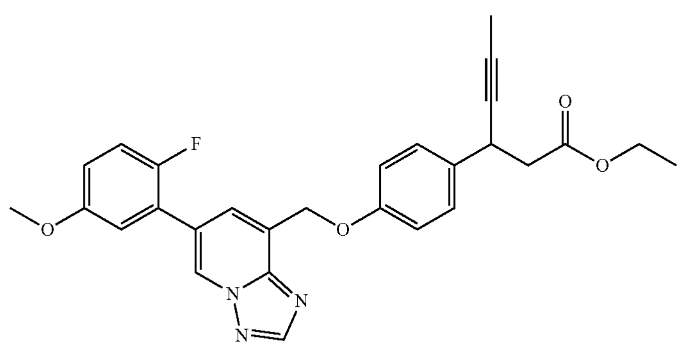 [SMILES: CC#CC(CC(=O)OCC)c1ccc(OCc2cc(-c3cc(OC)ccc3F)cn3ncnc23)cc1] | 488 |
| 34 | 3-{4-[6-(4-Methane sulfonyl-phenyl)-[1,2,4]triazolo[1,5-a]pyridin-8-ylmethoxy]-phenyl}-hex-4-ynoic acid ethyl ester | 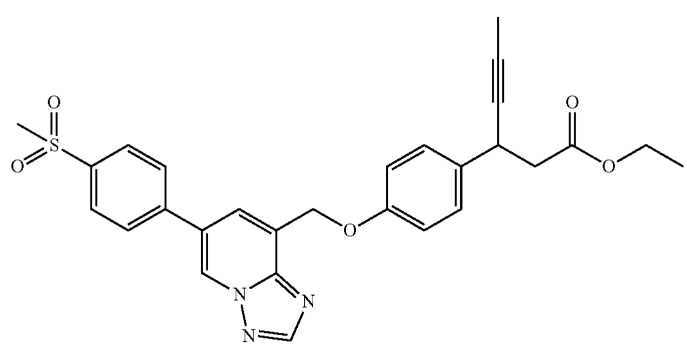 [SMILES: CC#CC(CC(=O)OCC)c1ccc(OCc2cc(-c3ccc(S(C)(=O)=O)cc3)cn3ncnc23)cc1] | 518 |

TABLE 7-continued

| Prep. No | Chemical Name | Structure | ES/MS (m/z) (M + 1) |
|---|---|---|---|
| 35 | (S)-3-{4-[6-(4-Formyl-phenyl)-[1,2,4]triazolo[1,5-a]pyridin-8-ylmethoxy]-phenyl}-hex-4-ynoic acid ethyl ester | 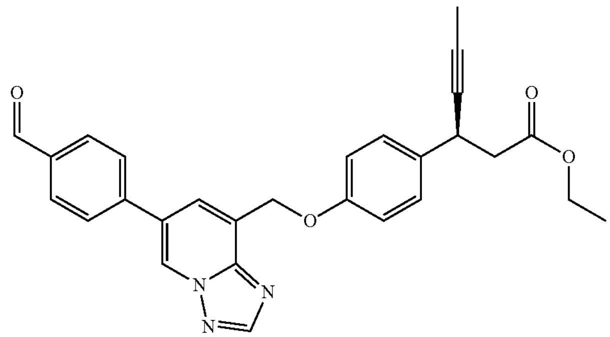 [SMILES: CC#C[C@@H](CC(=O)OCC)c1ccc(OCc2cc(-c3ccc(C=O)cc3)cn3ncnc23)cc1] | 468 |
| 36 | (S)-3-{4-[6-(2,6-Dimethyl-phenyl)-[1,2,4]triazolo[1,5-a]pyridin-8-ylmethoxy]-phenyl}-hex-4-ynoic acid ethyl ester | 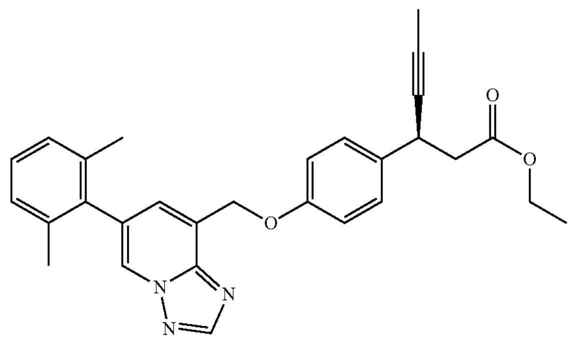 [SMILES: CC#C[C@@H](CC(=O)OCC)c1ccc(OCc2cc(-c3c(C)cccc3C)cn3ncnc23)cc1] | 468 |
| 37 | (S)-3-[4-(6-Bromo-[1,2,4]triazolo[1,5-a]pyridin-8-ylmethoxy)-phenyl]-hex-4-ynoic acid ethyl ester | 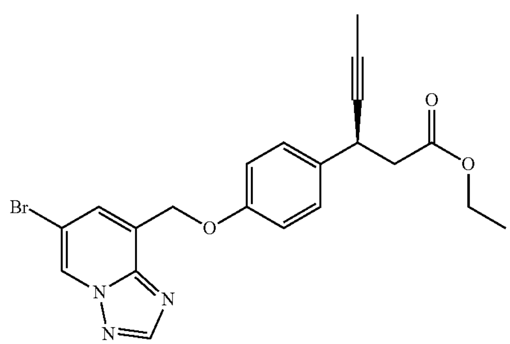 [SMILES: CC#C[C@@H](CC(=O)OCC)c1ccc(OCc2cc(Br)cn3ncnc23)cc1] | 442/444 |

Preparation 38

6-(4-Dimethoxymethyl-phenyl)-[1,2,4]triazolo[1,5-a]pyridine-8-carboxylic acid methyl ester

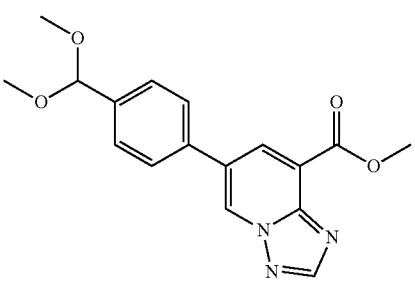

To a stirred solution of 6-(4-formyl-phenyl)-[1,2,4]triazolo[1,5-a]pyridine-8-carboxylic acid methyl ester (0.8 g, 2.84 mmol) in MeOH (20 mL) is added trimethylortho formate (4 mL) and p-toluenesulfonic acid (0.05 g) at 0° C. The reaction mixture is allowed to warm to room temperature and stirred for 1 hour. The reaction mixture is evaporated to dryness and purified on silica gel column chromatography with 30% EtOAc in hexanes (1.0 g, 100%). LCMS m/z 328 (M+H)+.

Preparation 39

4-(8-Bromomethyl-[1,2,4]triazolo[1,5-a]pyridin-6-yl)-benzaldehyde

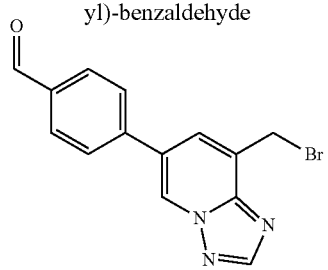

To a stirred solution [6-(4-dimethoxymethyl-phenyl)-[1,2,4]triazolo[1,5-a]pyridin-8-yl]-methanol (0.4 g, 1.33 mmol) in DCM (20 mL) is added triphenylphosphine (0.52 g, 1.9 mmol) and the mixture is cooled to 0° C. Carbon tetrabromide (0.66 g, 1.9 mmol) is added in portions and the mixture is stirred at room temperature overnight. The reaction mixture is evaporated to dryness and the material is purified on silica gel column chromatography with 30% EtOAc in hexanes to give the title compound (0.75 g, 59.5%).

$^1$H NMR (400 MHz, CDCl$_3$) δ 8.83 (s, 1H), 8.43 (s, 1H), 8.04 (d, J=8.4 Hz, 2H), 7.88 (s, 1H), 7.78 (d, J=8.4 Hz, 2H), 7.67 (s, 1H), 4.93 (s, 1H).

Preparation 40

(S)-3-{4-[6-(4-Difluoromethyl-phenyl)-[1,2,4]triazolo[1,5-a]pyridin-8-ylmethoxy]-phenyl}-hex-4-ynoic acid ethyl ester

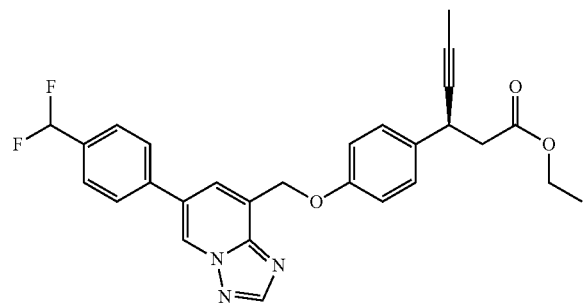 [SMILES: CC#C[C@@H](CC(=O)OCC)c1ccc(OCc2cc(-c3ccc(C(F)F)cc3)cn3ncnc23)cc1]

(S)-3-{4-[6-(4-Formyl-phenyl)-[1,2,4]triazolo[1,5-a]pyridin-8-ylmethoxy]-phenyl}-hex-4-ynoic acid ethyl ester (0.17 g, 0.36 mmol) is combined with diethylaminosulfur trifluoride (0.5 mL) in DCM (20 mL) at room temperature and the reaction mixture is stirred for 2 hours. The mixture is partitioned between water (20 mL) and DCM (50 mL) and the organic layer is isolated, dried, and evaporated under reduced pressure. The crude material is purified by silica gel column chromatography, eluting with 25% EtOAc in hexanes to give the title compound (0.11 g, 61.7%). LCMS m/z 490 (M+H)$^+$.

Preparation 41

(S)-3-(4-{6-[4-(Cyano-dimethyl-methyl)-phenyl]-[1,2,4]triazolo[1,5-a]pyridin-8-ylmethoxy}-phenyl)-hex-4-ynoic acid ethyl ester

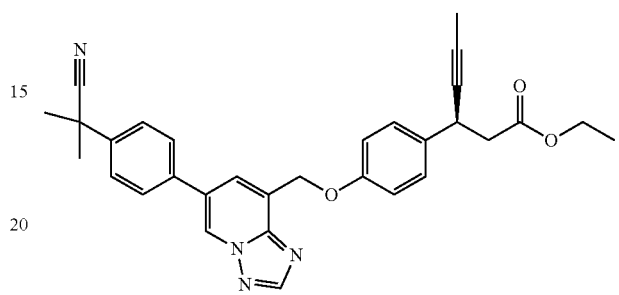

To a stirred solution of 2-methyl-2-[4-(4,4,5,5-tetramethyl-[1,3,2]dioxaborolan-2-yl)-phenyl]-propionitrile (0.24 g, 0.542 mmol) and (S)-3-[4-(6-bromo-[1,2,4]triazolo[1,5-a]pyridin-8-ylmethoxy)-phenyl]-hex-4-ynoic acid ethyl ester (0.157 g, 0.597 mmol) in 1,4-dioxane (10 mL) is added 2 M potassium carbonate (0.542 ml, 1.084 mmol) at room temperature. The reaction mixture is purged under nitrogen atmosphere for 20 minutes and Pd(PPh$_3$)$_2$Cl$_2$ (0.018 g, 0.0271 mmol) is added at room temperature.

The reaction mixture is heated at 100° C. for 1 hour. The reaction mixture is filtered through diatomaceous earth and washed with EtOAc (2×20 mL). The filtrate is washed with cold water (2×10 mL) and brine solution (10 mL), dried over anhydrous sodium sulphate, filtered and evaporated to dryness. The crude material is purified by silica gel column chromatography (combiflash) eluting with 20-50% EtOAc in hexanes to give the title compound as a pale yellow syrup (0.11 g, 40%). LC-MS m/z 507 [M+H]$^+$.

The following compounds are prepared essentially by the method of preparation 41.

TABLE 8

| Prep. No | Chemical Name | Structure | ES/MS (m/z) (M + 1) |
|---|---|---|---|
| 42 | (S)-3-{4-[6-(4-Cyano-phenyl)-[1,2,4]triazolo[1,5-a]pyridin-8-ylmethoxy]-phenyl}-hex-4-ynoic acid ethyl ester | 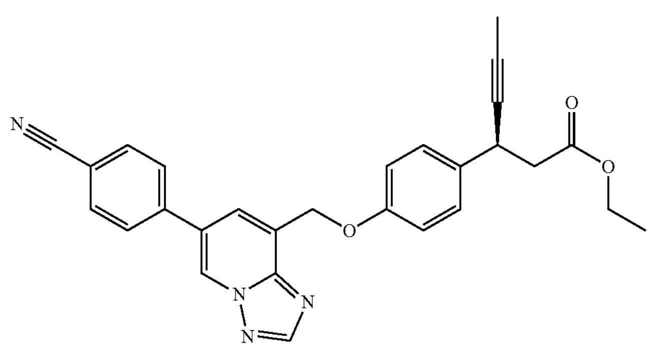 [SMILES: CC#C[C@@H](CC(=O)OCC)c1ccc(OCc2cc(-c3ccc(C#N)cc3)cn3ncnc23)cc1] | 465 |

TABLE 8-continued

| Prep. No | Chemical Name | Structure | ES/MS (m/z) (M + 1) |
|---|---|---|---|
| 45 | (S)-3-{4-[6-(2-Fluoro-6-methyl-phenyl)-[1,2,4]triazolo[1,5-a]pyridin-8-ylmethoxy]-phenyl}-hex-4-ynoic acid ethyl ester | 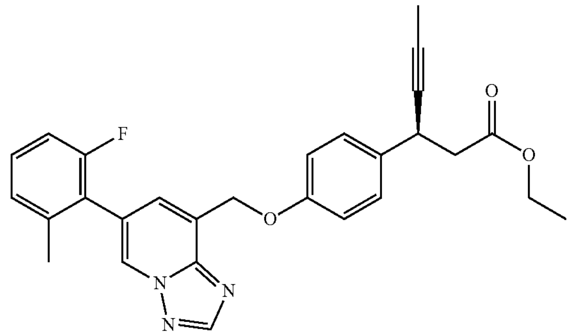 [SMILES: CC#C[C@@H](CC(=O)OCC)c1ccc(OCc2cc(-c3c(C)cccc3F)cn3ncnc23)cc1] | 472 |
| 46 | (S)-3-{4-[6-(2-Methyl-4-sulfamoyl-phenyl)-[1,2,4]triazolo[1,5-a]pyridin-8-ylmethoxy]-phenyl}-hex-4-ynoic acid ethyl ester | 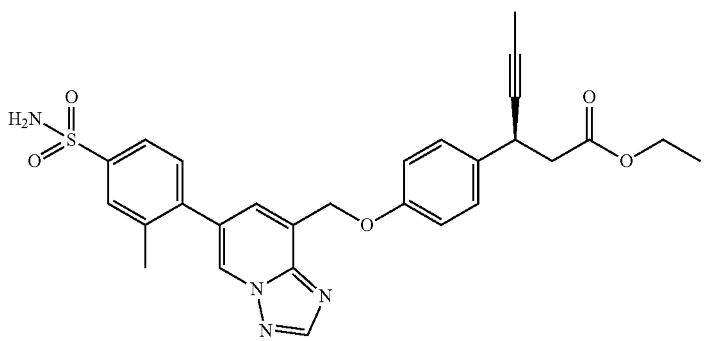 [SMILES: CC#C[C@@H](CC(=O)OCC)c1ccc(OCc2cc(-c3ccc(S(N)(=O)=O)cc3C)cn3ncnc23)cc1] | 533 |

Preparation 47

(S)-3-{4-[6-(5-Chloro-2-methyl-phenyl)-[1,2,4]triazolo [1,5-a]pyridin-8-ylmethoxy]-phenyl}-hex-4-ynoic acid ethyl ester

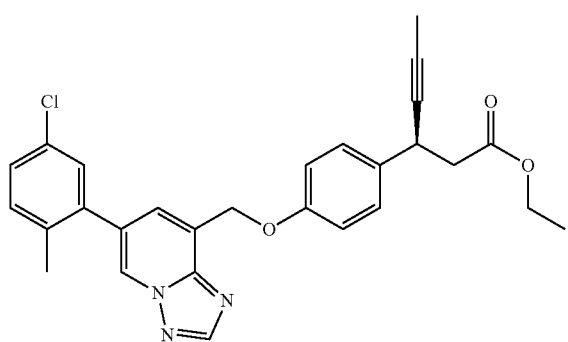 [SMILES: CC#C[C@@H](CC(=O)OCC)c1ccc(OCc2cc(-c3cc(Cl)ccc3C)cn3ncnc23)cc1]

To a stirred solution of (S)-3-[4-(6-bromo-[1,2,4]triazolo [1,5-a]pyridin-8-ylmethoxy)-phenyl]-hex-4-ynoic acid ethyl ester (0.25 g, 0.565 mmol) and 2-(5-chloro-2-methyl-phenyl)-4,4,5,5-tetramethyl-[1,3,2]dioxaborolane (0.142 g, 0.565 mmol) in dioxane (20 mL) is added 2 M $K_2CO_3$ (0.7 mL, 1.13 mmol). The mixture is purged with argon for 30 minutes, Pd(PPh$_3$)$_4$(0.032 g, 0.028 mmol) is added and the mixture is heated at 100° C. for overnight. The reaction mixture is cooled to room temperature and filtered through diatomaceous earth. The filtrate is diluted with water (30 mL) and extracted with EtOAc (2×20 mL). The combined organic extracts are washed with saturated brine solution (20 mL), dried over sodium sulphate, filtered, and concentrated. The crude material is purified by silica gel column chromatography (combiflash) eluting with 75% EtOAc/hexanes to obtain the title compound (0.15 g, 54%). LCMS m/z 488 (M+H)$^+$.

The following compounds are prepared essentially by the method of preparation 47.

TABLE 9

| Prep. No | Chemical Name | Structure | ES/MS (m/z) (M + 1) |
|---|---|---|---|
| 48 | (S)-3-{4-[6-(4-Hydroxy-2-methyl-phenyl)-[1,2,4]triazolo[1,5-a]pyridin-8-ylmethoxy]-phenyl}-hex-4-ynoic acid ethyl ester | 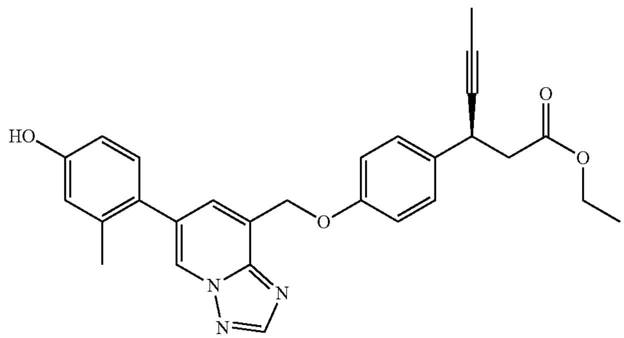 [SMILES: CC#C[C@@H](CC(=O)OCC)c1ccc(OCc2cc(-c3ccc(O)cc3C)cn3ncnc23)cc1] | 470 |
| 49 | (S)-3-{4-[6-(4-Methoxy-2-methyl-phenyl)-[1,2,4]triazolo[1,5-a]pyridin-8-ylmethoxy]-phenyl}-hex-4-ynoic acid ethyl ester | 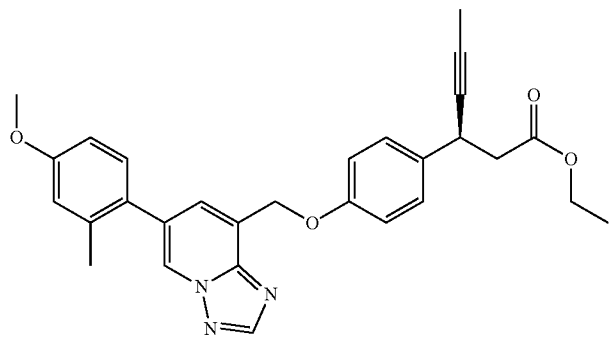 [SMILES: CC#C[C@@H](CC(=O)OCC)c1ccc(OCc2cc(-c3ccc(OC)cc3C)cn3ncnc23)cc1] | 484 |

Preparation 50

(S)-3-{4-[6-(4-Isopropyl-phenyl)-[1,2,4]triazolo[1,5-a]pyridin-8-ylmethoxy]-phenyl}-hex-4-ynoic acid ethyl ester

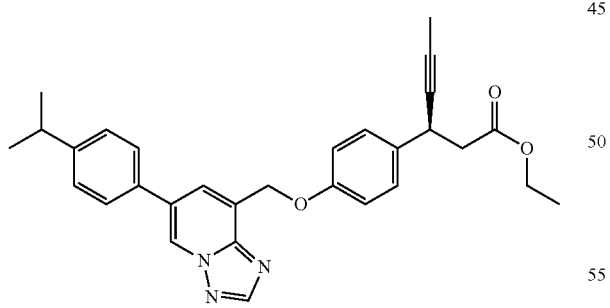

To a stirred solution of 3-[4-(6-bromo-[1,2,4]triazolo[1,5-a]pyridin-8-ylmethoxy)-phenyl]-hex-4-ynoic acid ethyl ester (0.25 g, 0.56 mmol) and 4-isopropyl-phenylboronic acid (0.28 g, 1.13 mmol) in toluene (12 mL) and EtOH (3 mL) is added 2 M $K_2CO_3$ (0.56 mL, 1.13 mmol). The mixture is purged with argon for 30 minutes, $Pd(PPh_3)_4$ (0.065 g, 0.05 mmol) is added, and the mixture is heated at 100° C. for 16 hours. The reaction mixture is cooled to room temperature and filtered through diatomaceous earth. The filtrate is diluted with water (20 mL) and extracted with EtOAc (2×20 mL). The combined organic extracts are washed with saturated brine solution (10 mL), dried over sodium sulphate, filtered, and concentrated. The crude material is purified by silica gel column chromatography (combiflash) eluting in 50% EtOAc/hexanes to give title compound as a yellow liquid (0.2 g, 73.52%). LCMS m/z 482 $(M+H)^+$.

Preparation 51

(S)-3-{4-[6-(4-Cyanomethoxy-2-methyl-phenyl)-[1,2,4]triazolo[1,5-a]pyridin-8-ylmethoxy]-phenyl}-hex-4-ynoic acid ethyl ester

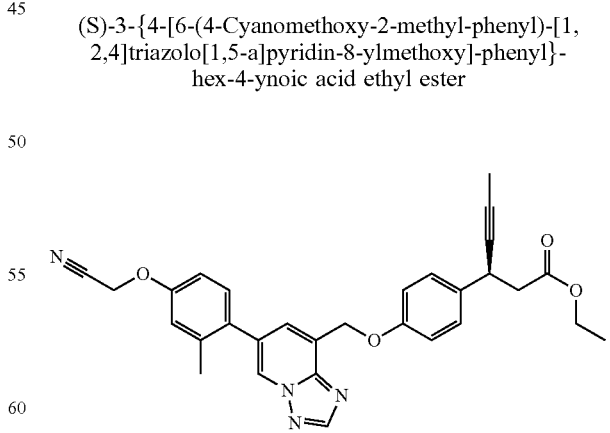

To a stirred solution of (S)-3-{4-[6-(4-hydroxy-2-methyl-phenyl)-[1,2,4]triazolo[1,5-a]pyridine-8-ylmethoxy]-phenyl}-hex-4-ynoic acid ethyl ester (0.25 g, 0.53 mmol) in acetonitrile (20 mL) is added bromoacetonitrile (0.319 g, 2.6 mmol) and potassium carbonate (0.146 g, 1.06 mmol) at room temperature. The reaction mixture is stirred at 100° C. for 4 hours. The reaction mixture is diluted with water (10 mL) and extracted with EtOAc (2×20 mL). The combined organic extracts are washed with water (10 mL) and brine (10 mL), dried over anhydrous sodium sulphate, filtered, and evaporated. The crude material is purified by silica gel column chromatography (combiflash) eluting with 60% EtOAc in hexanes to give the title compound as a colorless sticky solid (0.18 g, 66.6%). LC-MS m/z 509 [M+H]+.

Preparation 52

(S)-3-{4-[6-(4-Difluoromethoxy-2-methyl-phenyl)-[1,2,4]triazolo[1,5-a]pyridin-8-ylmethoxy]-phenyl}-hex-4-ynoic acid ethyl ester

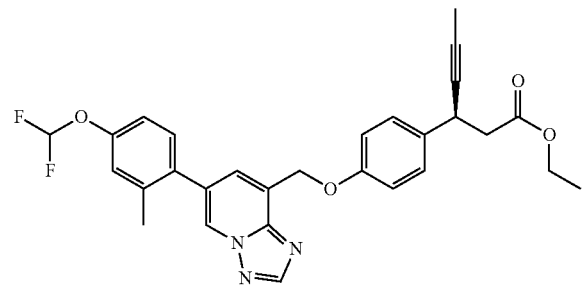 [SMILES: CC#C[C@@H](CC(=O)OCC)c1ccc(OCc2cc(-c3ccc(OC(F)F)cc3C)cn3ncnc23)cc1]

To a stirred solution of (S)-3-{4-[6-(4-difluoromethoxy-2-methyl-phenyl)-[1,2,4]triazolo [1,5-a]pyridin-8-ylmethoxy]-phenyl}-hex-4-ynoic acid ethyl ester (0.25 g, 0.53 mmol) in DMF (10 mL) is added 1-chloro-1,1-difluoroacetone (0.249 g, 1.5 mmol) and cesium carbonate (0.346 g, 1.06 mmol) at room temperature. The reaction mixture is stirred at 80° C. for 2 hours. The reaction mixture is diluted with water (10 mL) and extracted with EtOAc (3×20 mL). The combined organic layer is dried over anhydrous sodium sulphate, filtered, and evaporated to dryness. The crude material is purified by silica gel column chromatography, (combiflash) eluting with 50% EtOAc in hexanes to give the title compound as a colorless sticky solid (0.120 g, 66.6%). LC-MS m/z 520 [M+H]+.

Preparation 53

(S)-3-(4-{6-[4-(3-Methanesulfonyl-propoxy)-2-methyl-phenyl]-[2,4]triazolo 1,5-a]pyridin-8-yl-methoxy}-phenyl)-hex-4-ynoic acid ethyl ester

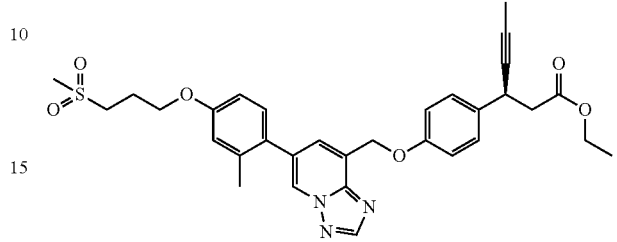

A mixture of (S)-3-{4-[6-(4-hydroxy-2-methyl-phenyl)-[1,2,4]triazolo[1,5-a]pyridin-8-ylmethoxy]-phenyl}-hex-4-ynoic acid ethyl ester (0.15 g, 0.31 mmol), toluene-4-sulfonic acid 3-methanesulfonyl-propyl ester (0.28 g, 0.95 mmol) and potassium carbonate (0.129 g, 0.95 mmol) in acetonitrile (15 mL) is stirred overnight at 80° C. The reaction mixture is diluted with water (50 mL) and extracted with EtOAc (2×30 mL). The combined organic extracts are washed with saturated brine solution (20 mL), dried over sodium sulphate, filtered, and evaporated to dryness. The crude material is purified by silica gel column chromatography (combiflash) eluting with 90% EtOAc/hexanes to obtain the title compound as an off white solid (0.15 g, 83.3%). LCMS m/z 590 (M+H)+.

Preparation 54 (S)-3-(4-{6-[4-(3-Hydroxy-3-methyl-butoxy)-2-methyl-phenyl]-[1,2,4]triazolo [1,5-a] pyridin-8-ylmethoxy}-phenyl)-hex-4-ynoic acid ethyl ester

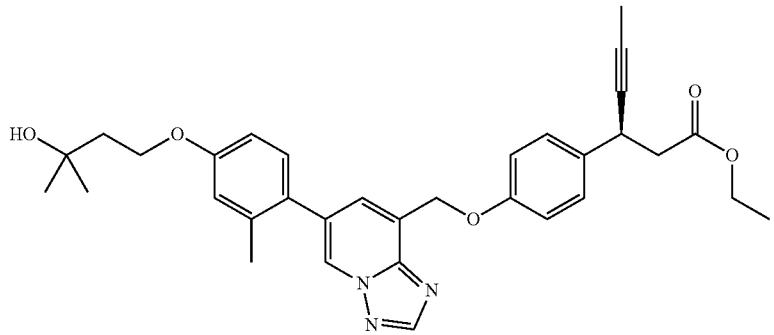 [SMILES: CC#C[C@@H](CC(=O)OCC)c1ccc(OCc2cc(-c3ccc(OCCC(C)(C)O)cc3C)cn3ncnc23)cc1]

A mixture of (S)-3-{4-[6-(4-hydroxy-2-methyl-phenyl)-[1,2,4]triazolo[1,5-a]pyridin-8-ylmethoxy]-phenyl}-hex-4-ynoic acid ethyl ester (0.1 g, 0.21 mmol), 4-bromo-2-methyl-butan-2-ol (0.106 g, 0.63 mmol) and cesium carbonate (0.136 g, 0.42 mmol) in acetonitrile (15 mL) is stirred at 80° C. for 4 hours. The reaction mixture is diluted with water (20 mL) and extracted with EtOAc (2×20 mL).

The combined organic layer is washed with saturated brine solution (20 mL), dried over sodium sulphate, filtered, and evaporated to dryness. The crude material is purified by silica gel column chromatography (combiflash) eluting with 70% EtOAc/hexanes to obtain title compound as a brown solid (0.09 g, 81.8%). LCMS m/z 556 (M+H)$^+$.

EXAMPLE 1

(S)-3-[4-(6-o-Tolyl-[1,2,4]triazolo[1,5-a]pyridin-8-ylmethoxy)-phenyl]-hex-4-ynoic acid

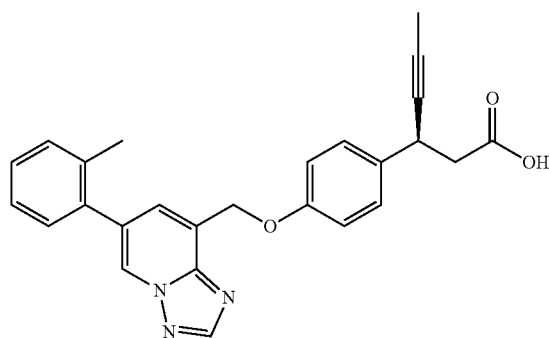 [SMILES: CC#C[C@@H](CC(=O)O)c1ccc(OCc2cc(-c3ccccc3C)cn3ncnc23)cc1]

To a stirred solution of (S)-3-[4-(6-o-tolyl-[1,2,4]triazolo[1,5-a]pyridin-8-ylmethoxy)-phenyl]-hex-4-ynoic acid ethyl ester (0.11 g, 0.23 mmol) in MeOH (4 mL) is added 5.0 M sodium hydroxide solution (0.23 mL, 1.17 mmol) at room temperature. The reaction mixture is stirred at room temperature for 3 hours. The reaction mixture is concentrated under reduced pressure. The obtained residue is triturated with diethyl ether (2×2 mL), dried, and diluted with water (5 mL). The aqueous solution is neutralized with citric acid (pH ~7). The precipitated solid is filtered and dried to give the title compound as a white solid (0.061 g, 49.3%). LCMS m/z 426.2 (M+H)$^+$. $^1$HNMR (400 MHz, CDCl$_3$) δ 12.1 (bs, 1H), 8.90 (s, 1H), 8.55 (s, 1H), 7.70 (s, 1H), 7.33-7.26 (m, 6H), 7.02 (d, J=8.4 Hz, 2H), 5.45 (s, 2H), 3.93 (m, 1H), 2.65 (d, J=7.6 Hz, 2H), 2.19 (s, 3H), 1.76 (s, 3H).

The following compounds are prepared essentially by the method of Example 1.

TABLE 10

| Ex. No | Chemical Name | Structure | ES/MS (m/z) (M + 1) |
|---|---|---|---|
| 2 | (S)-3-{4-[6-(4-Methoxy-phenyl)-[1,2,4]triazolo[1,5-a]pyridin-8-ylmethoxy]-phenyl}-hex-4-ynoic acid | 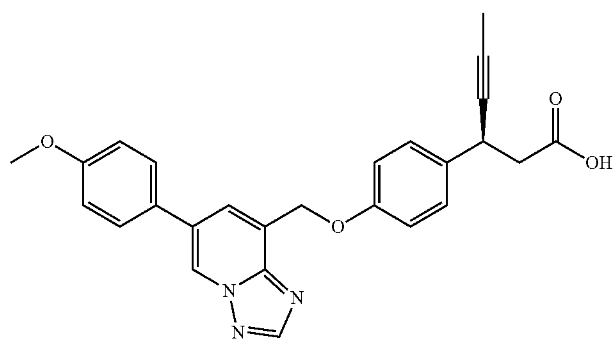 [SMILES: CC#C[C@@H](CC(=O)O)c1ccc(OCc2cc(-c3ccc(OC)cc3)cn3ncnc23)cc1] | 442 |
| 3 | (S)-3-{4-[6-(2-Fluoro-6-methyl-phenyl)-[1,2,4]triazolo[1,5-a]pyridin-8-ylmethoxy]-phenyl}-hex-4-ynoic acid | 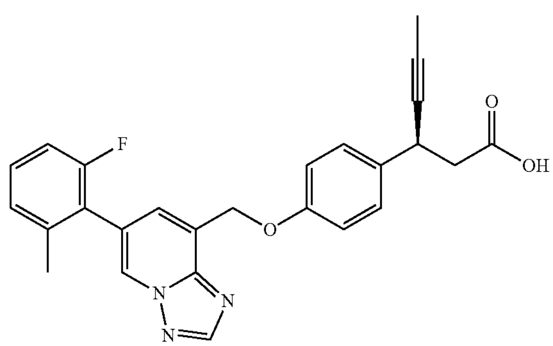 [SMILES: CC#C[C@@H](CC(=O)O)c1ccc(OCc2cc(-c3c(C)cccc3F)cn3ncnc23)cc1] | 444 |

Alternate Preparation Example 1

To a stirred solution of (S)-3-[4-(6-o-tolyl-[1,2,4]triazolo[1,5-a]pyridin-8-ylmethoxy)-phenyl]-hex-4-ynoic acid ethyl ester (458 g, 1.01 mol) in EtOH (9.1 L) is added a solution of sodium hydroxide (201.9 g, 5.04 mol) in water (2 L) over a period of 20 minutes at 0-10° C. The reaction mixture is warmed to 25° C. and stirred for 4 hours. The mixture is concentrated to dryness, dissolved in water (4 L), and stirred for 1 hour. A clear solution is obtained. DCM (4 L) is added and the mixture is stirred for 15 minutes. An emulsion resulted and the mixture is concentrated to a volume of about 4.5 L. The solution is washed with diethyl ether (3×2.5 L). The aqueous layer is isolated and cooled to 0° C. The pH is adjusted to 4.7 by adding saturated citric acid solution. The mixture is stirred for 1 hour, filtered, and washed with water (4×10 L) to give an off white solid. The material is re dissolved in EtOAc (5 L), filtered, and concentrated to give the title compound (321.6 g, 75%). LCMS m/z 426.2 (M+H)$^+$.

EXAMPLE 4

(S)-3-{4-[6-(4-Methoxy-2-methyl-phenyl)-[1,2,4]triazolo[1,5-a]pyridin-8-ylmethoxy]-phenyl}-hex-4-ynoic acid To a solution of (S)-3-{4-[6-(4-methoxy-2-methyl-phenyl)-[1,2,4]triazolo[1,5-a]pyridin-8-ylmethoxy]-phenyl}-hex-4-ynoic acid ethyl ester (0.29 g, 0.6 mmol) in EtOH (15 mL) is added 5 N NaOH (0.3 mL, 1.8 mmol). The mixture is stirred at room temperature for 2 hours. The mixture is evaporated to dryness, the residue is washed with pentane, dried and re-dissolved in water (5 mL). The solution is acidified with saturated citric acid solution to about pH 5. The solid precipitated is filtered, washed with water, and dried to give the title compound as an off white solid (0.115 g, 42.5%). LCMS m/z 455 (M+H)+; $^1$H NMR (400 MHz, DMSO) δ 12.18 (bs, 1H), 8.87 (s, 1H), 8.53 (s, 1H), 7.66 (s, 1H), 7.28-7.23 (m, 3H), 7.01-6.99 (d, J=5.6 Hz, 2H), 6.87 (s, 1H), 6.86-6.84 (d, J=8.0 Hz, 1H), 5.73 (s, 2H), 3.95 (s, 1H), 3.77 (s, 3H), 2.57-2.56 (d, J=7.2 Hz, 2H), 2.17 (s, 3H), 1.76 (s, 3H); HPLC Purity-99.43%.

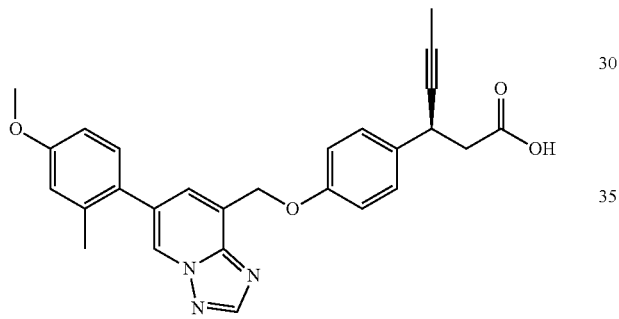

The following compounds are prepared essentially by the method of Example 4.

TABLE 11

| Ex. No | Chemical Name | Structure | ES/MS (m/z) (M + 1) |
|---|---|---|---|
| 5 | (S)-3-{4-[6-(4-Methoxy-2,6-dimethyl-phenyl)-[1,2,4]triazolo[1,5-a]pyridin-8-ylmethoxy]-phenyl}-hex-4-ynoic acid | 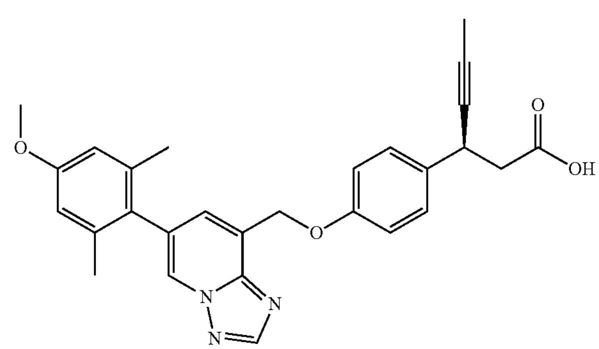 [SMILES: CC#C[C@@H](CC(=O)O)c1ccc(OCc2cc(-c3c(C)cc(OC)cc3C)cn3ncnc23)cc1] | 470 |

TABLE 11-continued

| Ex. No | Chemical Name | Structure | ES/MS (m/z) (M + 1) |
|---|---|---|---|
| 6 | (S)-3-{4-[6-(5-Methoxy-2-methyl-phenyl)-[1,2,4]triazolo[1,5-a]pyridin-8-ylmethoxy]-phenyl}-butyric acid | 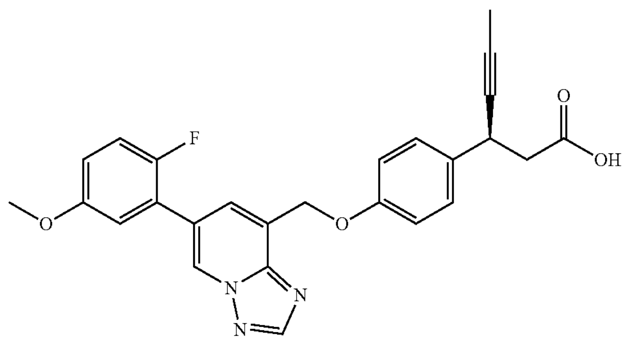 [SMILES: CC#C[C@@H](CC(=O)O)c1ccc(OCc2cc(-c3cc(OC)ccc3F)cn3ncnc23)cc1] | 460 |
| 7 | (S)-3-(4-{6-[4-(3-Methanesulfonyl-propoxy)-2-methyl-phenyl]-[1,2,4]triazolo[1,5-a]pyridin-8-ylmethoxy}-phenyl)-hex-4-ynoic acid | 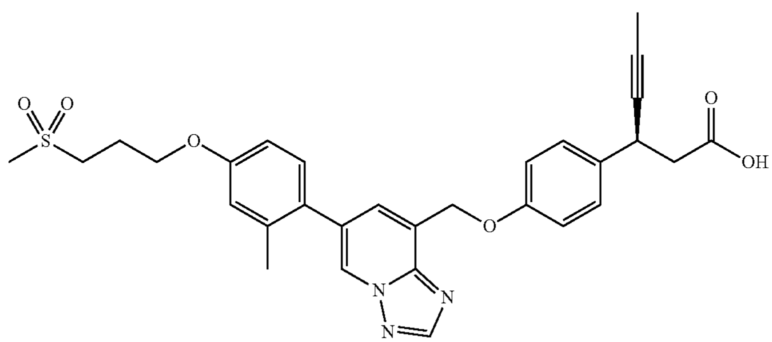 [SMILES: CC#C[C@@H](CC(=O)O)c1ccc(OCc2cc(-c3ccc(OCCCS(C)(=O)=O)cc3C)cn3ncnc23)cc1] | 562 |
| 8 | (S)-3-(4-{6-[4-(3-Hydroxy-3-methyl-butoxy)-2-methyl-phenyl]-[1,2,4]triazolo[1,5-a]pyridin-8-ylmethoxy}-phenyl)-hex-4-ynoic acid | 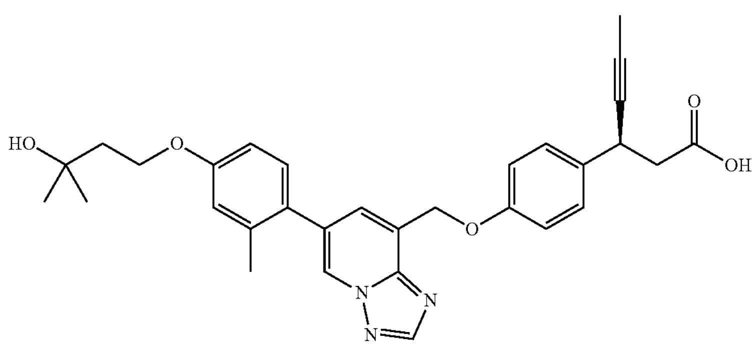 [SMILES: CC#C[C@@H](CC(=O)O)c1ccc(OCc2cc(-c3ccc(OCCC(C)(C)O)cc3C)cn3ncnc23)cc1] | 528 |
| 9 | (S)-3-{4-[6-(4-Isopropyl-phenyl)-[1,2,4]triazolo[1,5-a]pyridin-8-ylmethoxy]-phenyl}-hex-4-ynoic acid | 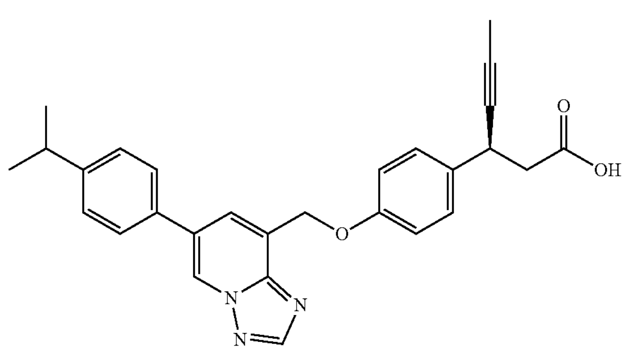 [SMILES: CC#C[C@@H](CC(=O)O)c1ccc(OCc2cc(-c3ccc(C(C)C)cc3)cn3ncnc23)cc1] | 454 |

TABLE 11-continued

| Ex. No | Chemical Name | Structure | ES/MS (m/z) (M + 1) |
|---|---|---|---|
| 11 | (S)-3-{4-[6-(2,6-Dimethyl-phenyl)-[1,2,4]triazolo[1,5-a]pyridin-8-ylmethoxy]-phenyl}-hex-4-ynoic acid | 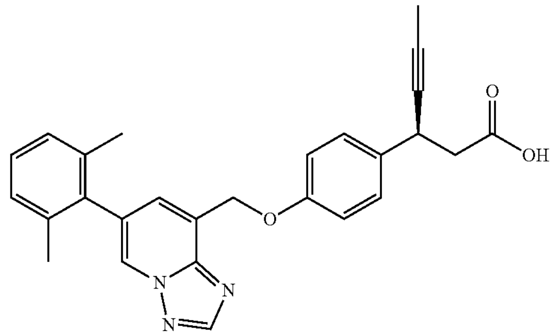 [SMILES: CC#C[C@@H](CC(=O)O)c1ccc(OCc2cc(-c3c(C)cccc3C)cn3ncnc23)cc1] | 439 |
| 12 | (S)-3-{4-[6-(6-Methoxy-pyridin-3-yl)-[1,2,4]triazolo[1,5-a]pyridin-8-ylmethoxy]-phenyl}-hex-4-ynoic acid | 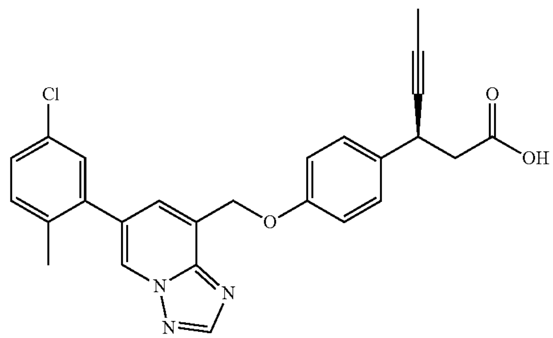 [SMILES: CC#C[C@@H](CC(=O)O)c1ccc(OCc2cc(-c3cc(Cl)ccc3C)cn3ncnc23)cc1] | 460 |

EXAMPLE 13

(S)-3-{4-[6-(4-Cyano-phenyl)-[1,2,4]triazolo[1,5-a]pyridin-8-ylmethoxy]-phenyl}-hex-4-ynoic acid

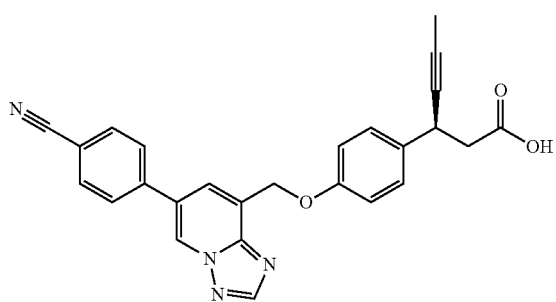 [SMILES: CC#C[C@@H](CC(=O)O)c1ccc(OCc2cc(-c3ccc(C#N)cc3)cn3ncnc23)cc1]

To a stirred solution of (S)-3-{4-[6-(4-cyano-phenyl)-[1,2,4]triazolo[1,5-a]pyridin-8-ylmethoxy]-phenyl}-hex-4-ynoic acid ethyl ester (0.1 g, 0.21 mmol) in dichloroethane (10 mL) is added trimethyltin hydroxide (0.19 g, 1.04 mmol) at room temperature. The reaction mixture is refluxed for overnight. The mixture is concentrated and purified on silica gel column chromatography with 3% MeOH in DCM to give the title compound as white solid (0.03 g, 32%). LCMS m/z 437.4 (M+H)+; $^1$HNMR (400 MHz, d$_6$-DMSO) δ 12.1 (bs, 1H), 9.46 (s, 1H), 8.60 (s, 1H), 8.16 (s, 1H), 8.04-7.96 (m, 4H), 7.29 (d, J=8.8 Hz, 2H), 7.04 (d, J=8.8 Hz, 2H), 5.46 (s, 2H), 3.94 (bs, 1H), 2.57 (d, J=7.6 Hz, 2H), 1.76 (s, 3H).

The following compounds are prepared essentially by the method of Example 13.

TABLE 12

| Ex. No | Chemical Name | Structure | ES/MS (m/z) (M + 1) |
|---|---|---|---|
| 15 | (S)-3-{4-[6-(4-Difluoromethyl-phenyl)-[1,2,4]triazolo[1,5-a]pyridin-8-ylmethoxy]-phenyl}-hex-4-ynoic acid | 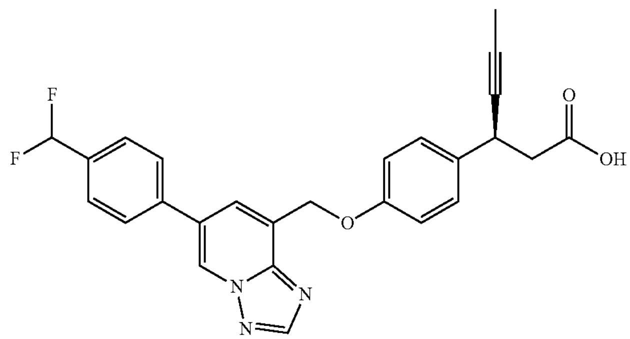 [SMILES: CC#C[C@@H](CC(=O)O)c1ccc(OCc2cc(-c3ccc(C(F)F)cc3)cn3ncnc23)cc1] | 462 |
| 16 | (S)-3-{4-[6-(4-Cyanomethoxy-2-methyl-phenyl)-[1,2,4]triazolo[1,5-a]pyridin-8-ylmethoxy]-phenyl}-hex-4-ynoic acid | 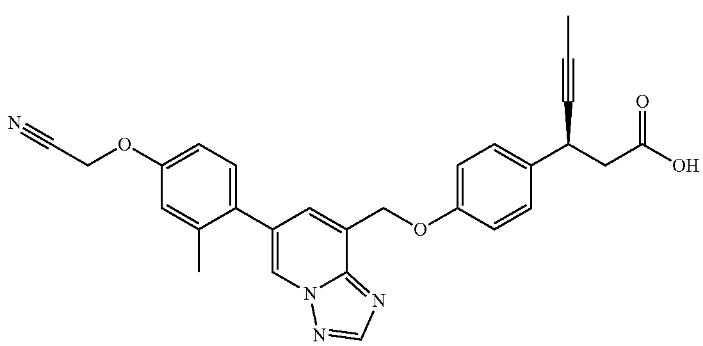 [SMILES: CC#C[C@@H](CC(=O)O)c1ccc(OCc2cc(-c3ccc(OCC#N)cc3C)cn3ncnc23)cc1] | 480 |

EXAMPLE 17

(S)-3-{4-[6-(4-Methanesulfonyl-phenyl)-[1,2,4]triazolo[1,5-a]pyridin-8-ylmethoxy]-phenyl}-butyric acid

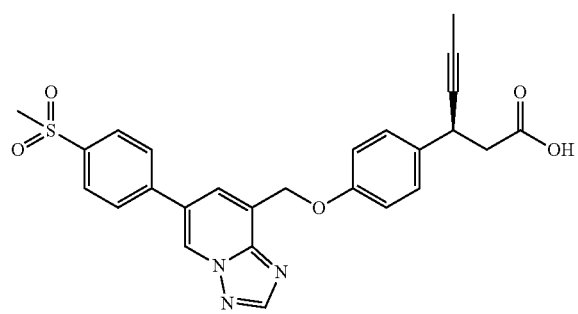 [SMILES: CC#C[C@@H](CC(=O)O)c1ccc(OCc2cc(-c3ccc(S(C)(=O)=O)cc3)cn3ncnc23)cc1]

To a solution of 3-{4-[6-(4-methanesulfonyl-phenyl)-[1,2,4]triazolo[1,5-a]pyridin-8-ylmethoxy]-phenyl}-hex-4-ynoic acid ethyl ester (0.07 g, 0.15 mmol) in THF:$H_2O$ (7:3, 5 mL), is added 3 M LiOH (0.012 mL, 0.2 mmol) at room temperature and the mixture is stirred for 3 hours. The mixture is evaporated to dryness and the residue is washed with pentane, dried and re-dissolved in water (5 mL). The solution is acidified with saturated citric acid solution to about pH 5. The solid precipitated is filtered, washed with water and dried to give the title compound as white solid (0.047 g, 70.1%). LCMS m/z 490 (M+H)+; $^1$H NMR (400 MHz, $d_6$-DMSO) δ 12.2 (bs, 1H), 9.46 (s, 1H), 8.60 (s, 1H), 8.16 (s, 1H) 8.08 (d, J=8.0 Hz, 2H), 8.03 (d, J=8.0 Hz, 2H), 7.29 (d, J=8.4 Hz, 2H), 7.04 (d, J=8.0 Hz, 2H), 5.47 (s, 2H), 3.94 (m, 1H), 2.5 (m, 2H), 1.76 (s, 3H); Purity HPLC: 95.832%.

The following compounds are prepared essentially by the method of Example 17.

TABLE 13

| Ex. No | Chemical Name | Structure | ES/MS (m/z) (M + 1) |
|---|---|---|---|
| 18 | (S)-3-{4-[6-(2-Methyl-4-sulfamoyl-phenyl)-[1,2,4]triazolo[1,5-a]pyridin-8-ylmethoxy]-phenyl}-hex-4-ynoic acid | 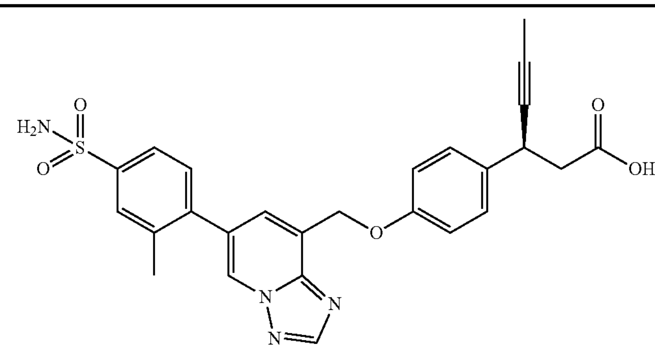 | 505 |
| 19 | (S)-3-(4-{6-[4-(Cyano-dimethyl-methyl)-phenyl]-[1,2,4]triazolo[1,5-a]pyridin-8-ylmethoxy}-phenyl)-hex-4-ynoic acid | 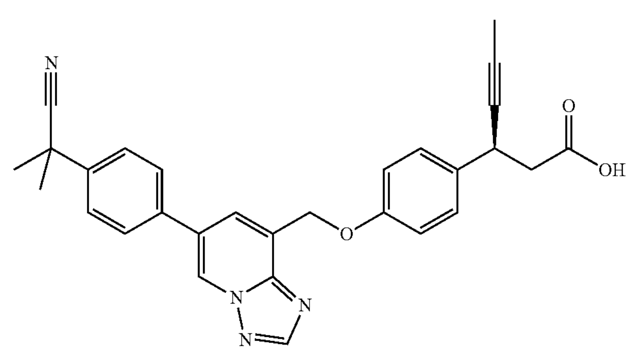 [SMILES: CC#C[C@@H](CC(=O)O)c1ccc(OCc2cc(-c3ccc(C(C)(C)C#N)cc3)cn3ncnc23)cc1] | 479 |

EXAMPLE 20

(S)-3-{4-[6-(4-Difluoromethoxy-2-methyl-phenyl)-[1,2,4]triazolo[1,5-a]pyridin-8-ylmethoxy]-phenyl}-hex-4-ynoic acid

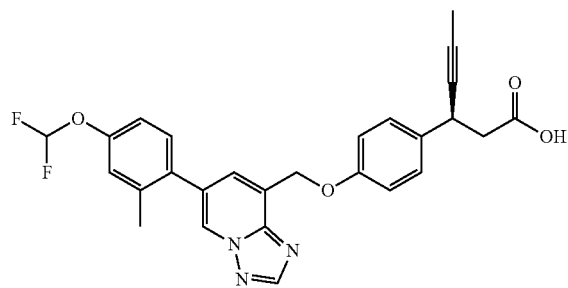 [SMILES: CC#C[C@@H](CC(=O)O)c1ccc(OCc2cc(-c3ccc(OC(F)F)cc3C)cn3ncnc23)cc1]

To a stirred solution of(S)-3-{4-[6-(4-difluoromethoxy-2-methyl-phenyl)-[1,2,4]triazolo[1,5-a]pyridin-8-ylmethoxy]-phenyl}-hex-4-ynoic acid (0.120 g, 0.23 mmol) in toluene:water (8:2, 5 mL) is added lithium hydroxide (0.029 g, 0.69 mmol) and the mixture is stirred at room temperature for 5 hours. The reaction mixture is evaporated under reduced pressure to give a solid and the solid is washed with n-pentane (3×5 mL), neutralized with citric acid solution (10 mL), and filtered to give the title compound as an off white solid (0.030 g, 25%). LCMS m/z 492 (M+H)+; $^1$H NMR (400 MHz, $d_6$-DMSO) δ 12.2 (bs, 1H), 8.99 (s, 1H), 8.58 (s, 1H), 7.68 (s, 1H), 7.45 (s, 1H), 7.39-7.37 (d, J=8.4 Hz, 1H), 7.28-7.26 (m, 2H), 7.17 (s, 1H), 7.12-7.08 (m, 1H), 7.03-6.99 (d, J=14.4 Hz, 2H), 5.45 (s, 2H), 3.94 (s, 1H), 2.58-2.56 (d, J=7.2 Hz, 2H), 2.20 (s, 3H), 1.76-1.76 (s, 3H), 1.22 (s, 2H); Purity by HPLC: 98.42%.

GPR40: Information

Results of studies using transgenic mice over-expressing the human GPR40 gene under control of the insulin II promoter recently reported by Nagasumi further support that GPR40 plays an important role in the regulation of GDIS and plasma glucose levels in-vivo, especially in rodent models of insulin resistance. Nagasumi K, et. al., Overexpression of GPR40 in pancreatic β-cells augments glucose-stimulated insulin secretion and improves glucose tolerance in normal and diabetic mice, *Diabetes* 58: 1067-1076, 2009. See also, Briscoe C P et al., The orphan G protein-coupled receptor GPR40 is activated by medium and long chain fatty acids, *Journal Biological Chemistry* 278: 11303-11311, 2003. These findings further support that the development of new GPR40 modulator compounds may be particularly desired for use in the treatment of T2D.

Assays

Calcium Flux Primary Assays

Examples 1 through 20 are tested essentially as described below.

These assays are used to screen compounds by measuring the increase in intracellular calcium levels that results when a ligand binds and activates GPR40, thus demonstrating the potency and efficacy of GPR40 agonists. HEK293 cells over expressing the human GPR40 cDNA maintained in Dulbecco's modified Eagle's medium with F12 medium in 3:1 ratio supplemented with 10% FBS and 800 µg/ml geneticin at 37° C. and 5% $CO_2$ are employed for the study. Agonist assays are performed using a Calcium 4 Dye assay kit (Molecular Devices) in the presence or absence of 0.1% fatty acid free BSA in the assay buffer (1×HBSS (Hank's Balanced Salt Solution) & 20 mM HEPES (4-(2-hydroxyethyl)-1-piperazineethanesulfonic acid). Receptor activation is measured as an increase in intracellular calcium using the Fluorometric Imaging Plate Reader (FLIPR). Maximum change in fluorescence over the base line is used to determine the agonist response. The $EC_{50}$ value of the compound is calculated using Excel Fit software (version 4; IDBS) by plotting concentration vs relative fluorescence units (RFUs). Percent efficacy is calculated based on the maximal response exhibited by compound compared to the natural ligand, linoleic acid. The test compound of Example 1 has an $EC_{50}$ of 146 nM (±15.4, n=6) and 70.5% efficacy (±0.821, n=2) when examined in this assay. These results further demonstrate the desired potency and efficacy of this compound as a GPR40 agonist. (Mean±SEM; SEM=standard error of the mean.) Examples 1 through 20 exhibit an $EC_{50}$ value for the Calcium Flux Primary assay of lower than 500 nM, and exhibited efficacy of >35%.

Selectivity Assays

Peroxisome Proliferator-Activated Receptor (PPAR) α, δ, and γ Functional Assays Because GPR40 is known to be activated by ligands to PPARγ, exemplified compounds are examined in Gal4 PPARα, Gal4 PPARδ, and PPARγ reporter assays to determine the selectivity of exemplified compounds for PPAR receptors. CV1 cells, which are derived from the renal tissue of an African green monkey, are transfected with various receptor and reporter plasmids using Fugene. For the Gal4 PPARα and PPARδ assays, a reporter plasmid containing five tandem copies of the yeast transcription protein Gal4 response element, cloned upstream of a firefly luciferase gene driven by the major late promoter of adenovirus, is transfected together with a Simian Virus 40 (SV40) driven plasmid constitutively expressing a hybrid protein containing the Gal4 DNA binding domain (DBD), and either the PPARα or PPARδ ligand binding domain. For the PPARγ assay, plasmids encoding PPARγ and RXRα, both driven by a cytomegalovirus (CMV) promoter are transfected together with a plasmid containing luciferase reporter cDNA driven by the TK promoter and a receptor response element (2×PPRE). Cells are transfected in T225 cm$^2$ cell culture flasks in DMEM media with 5% charcoal-stripped FBS and the specific plasmids for the individual assay. After an overnight incubation, transfected cells are trypsinized, plated in opaque 96 well dishes (15,000 cells/well) in DMEM media containing 5% charcoal-stripped FBS, incubated for 4 hours, and exposed to 0.17 ηM to 10 µM of test compounds or reference compound in half log dilutions. After 24 hours incubation with compounds, cells are lysed and luciferase activity is determined as a measure of receptor activation by luminescence. Data are fitted to a four parameter-fit logistics model to determine $EC_{50}$ values. The maximum percent stimulation is determined versus maximum stimulation obtained with 10 µM of an appropriate PPAR agonist reference compound, 2-methyl-2-(4-{2-methyl-3-[2-(phenylcarbonyl)-4-(trifluoromethoxy)phenoxy]propoxy}phenoxy)propanoic acid. Efficacy of <20% is considered negative. Efficacy was negative for PPARα, PPARδ, and PPARγ is detected with the compound of Example 1 when examined up to 10 M in the specific PPAR co-transfection (CTF) functional assays described above. Thus, these assays support that the exemplified compounds are negative for PPAR efficacy, as desired.

IN Vitro Binding Affinity to GPR40

Radioligand competition binding assays using rapid-wash filtration with a custom prepared radiolabel (5 nM [$^3$H] (TAK-875)) and membranes prepared from HEK293 cells overexpressing the human GPR40 (hGPR40) construct are run to determine equilibrium dissociation constants ($K_i$) for test compounds. Competition curves are plotted as the percent specific inhibition versus concentration of compound and analyzed using a four parameter nonlinear regression fit with variable slope. $K_i$ values are calculated using the Cheng-Prusoff equation $K_i=IC_{50}/(1+(D/K_d))$, where $IC_{50}$ is the concentration of compound resulting in 50% inhibition of binding, D is the concentration of radioligand used in the assay and $K_d$ is the equilibrium dissociation constant for the receptor and the radioligand, determined from saturation binding analysis experiments ($K_d$ for [$^3$H] TAK-875=6.2). See Cheng, Y. and Prusoff, W. H. (1973) "Relationship between the inhibition constant ($K_i$) and the concentration of inhibitor which causes 50 percent inhibition ($IC_{50}$) of an enzymatic reaction," *Biochem Pharmacol* 22(23):3099-3108. (Mean±SEM; SEM=standard error of the mean.). For Example 1, $K_i$=24.6 nM±4.51, n=6. These data demonstrate that the Example 1 compound is a high affinity ligand for human GPR40.

Human and Mouse Beta-Arrestin Agonist Assay with 1% FBS to Determine Beta-Arrestin Recruitment Human embryonic kidney (hEK293)-hFFAR1 cells are purchased from DiscoveRx. Human osteosarcoma (U2OS) cells expressing mFFAR1 are developed by DiscoveRX. These cells co-express the Prolink (PK)-tagged GPR40 and the Enzyme Acceptor (EA)-tagged beta-arrestin fusion proteins. If activation of the GPR40 stimulates beta-arrestin recruitment, it would force complementation of the beta galactosidase (B-gal) enzyme fragments, forming a B-gal enzyme that generates a chemiluminescent signal using the DiscoveRx PathHunter detection kit. Cells are incubated overnight at 5,000 cells/well in 384 well plates in culture media containing 1% FBS (fetal bovine serum). Serial diluted compounds in DMSO (2× dilutions to generate 20 concentrations) are step down diluted in culture media containing 1% FBS (fetal bovine serum) and added to cells with a final top concentration starting of 100 μM. After addition of compounds, cells are incubated for 90 min at 37° C. in 5% $CO_2$ incubator, and DiscoveRX kit detection reagents are added. Measurement of the chemiluminescent signal is ascertained with the Envision reader, after a 1-hour incubation at room temperature. Data are fit to a 4 parameter-fit logistics to determine $EC_{50}$ values; % activity is measured versus maximum response to TAK875 at 1 μM. For hGPR40 b-arrestin, Example 1 has an $EC_{50}$ of 47.4 nM (±14.4, n=4) with a % stimulation max (FA) of 163 (±11.3, n=4) and mGPR40 b-arrestin of 4.02 nM (±1.97, n=5) with a % stimulation max (FA) of 160 (±7.71, n=5). (Mean±SEM; SEM=standard error of the mean.) These data indicate that the compound of Example 1 is a GPR40 agonist which can signal through the beta arrestin pathway.

Acute Oral Glucose Tolerance Test (OGTT) in Zucker fa/fa Rats

OGTTs are performed in Zucker fa/fa rats, a rodent model of insulin resistance, after 1 and 21 days of orally administered material at 1.0, 3.0 and 10 mg/kg. TAK875 at 1 mg/kg served as the positive control. The OGTTs are performed one hour post compound administration with blood samples taken for determination of glucose and insulin levels at 10, 20, 40, 60, and 120 minutes post glucose administration. The AUCs for glucose lowering were statistically significant (p<0.05) for all doses of compound of Example 1 tested (1, 3, and 10 mg/kg) and with the positive control. Insulin AUCs demonstrated a dose dependent elevation during the OGTTs; although, these values were not statistically significant. The $ED_{90}$ for glucose lowering is 3.3 mg/kg. These findings demonstrate that glucose lowering activity is observed in Zucker fa/fa rats following oral administration with Example 1.

In Vivo Efficacy: Intraperitoneal Glucose Tolerance Test (IPGTT)

To examine the ability of Examples 1 to 20 to activate GPR40 in-vivo resulting in desired glucose lowering efficacy, i.e. reduction in plasma glucose levels, an intraperitoneal glucose tolerance test (ipGTT) study is completed, and the data is shown for the compound tested below.

Male Balb/c (Albino mice) mice (8-9 weeks of age) are single housed, and fed with normal rodent chow diet and water ad libitum. Animals are weighed; randomized by body weight; and their daily body weights are recorded. Animals are dosed daily using a formulation carrying methylcellulose and tween-80. On the night before the study, animals are fasted. In the morning, animals are dosed orally with compound or vehicle alone 60 minutes prior to the glucose tolerance test (glucose 2 g/kg, i.p.). Blood glucose levels are determined from tail bleeds taken at 0, 3, 7, 15, 30, and 60 min after glucose challenge. The blood glucose excursion profile from t=0 to t=60 min is used to integrate an area under the curve (AUC) for each treatment. Percent lowering in glucose is calculated from the AUC data of the compound with respect to the AUC of vehicle group. The test compound is orally administered at 0.3, 1.0, 3.0, 10, 30, or 100 mg/kg, and a positive control (3-[4-(2-methyl-benzyloxy)-phenyl]-hex-4-ynoic acid, see WO2005086661 (TAK875).) is administered at 10 mg/kg. Glucose levels are significantly lowered compared to those achieved with the vehicle control at the 30 and 60 minute time points with the 10, 30, and 100 mg/kg doses of Example 1. Glucose levels are lowered at the 30, and 60 minute time points for the positive control. The $ED_{50}$ for this compound based on AUCs for glucose lowering is 7.9 mg/kg. Results from this study demonstrate that activation of GPR40 by Example 1 leads to in-vivo antidiabetic efficacy.

The exemplified compounds of the present invention can be readily formulated into pharmaceutical compositions in accordance with accepted practices known in the art such as found in Remington's "Pharmaceutical Sciences", Gennaro, Ed., Mack Publishing Co. Easton Pa. 1990 such as tablets, solid or gel filled capsules, powders, suspensions, or solutions. The composition can also include one or more pharmaceutically acceptable carriers, excipients, and diluents.

Preferred pharmaceutical compositions are formulated as a tablet or capsule for oral administration. The tablet or capsule can include a compound of the present invention in an amount effective to treat diabetes, particularly type two diabetes. The artisan will appreciate that a compound of Formula I may be administered with one or more additional therapeutic agents. It may be preferred that pharmaceutical compositions are formulated to include a compound of Formula I and one or more additional therapeutic agents. An additional therapeutic agent is, for example, metformin.

The pharmaceutical composition is administered to a patient in amounts effective to treat diabetes, more particularly, type two diabetes. As used herein "effective amount" means an appropriate amount or dose effective to treat a patient as determined by a health care provider. Generally, an appropriate dose will contain more than about 1 ng/kg to less than about 100 mg/kg of a compound of the present invention.

What is claimed is:

1. A compound of the formula:

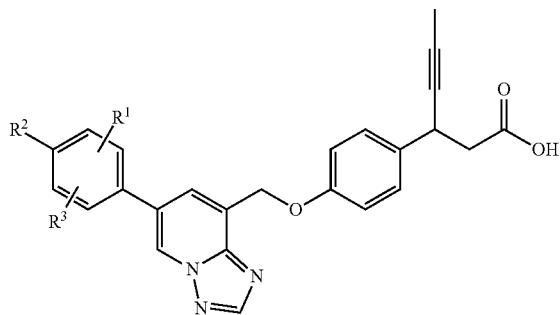

wherein
$R^1$ is selected from the group consisting of H, $CH_3$, CN, —$CH_2CN$, —$C(CH_3)_2CN$, F, Cl, and Br;
$R^2$ is selected from the group consisting of H, —O($C_1$-$C_3$alkylene)$R^4$, —$CH_2CN$, CN, —$OCH_3$, $CF_2$, —$C(CH_3)_2CN$, —$C(CH_3)_2$, —$S(O)_2CH_3$, —$S(O)_2NH_2$, and —$OCF_2$;
$R^3$ is selected from the group consisting of H, $CH_3$, and —$OCH_3$; and
$R^4$ is selected from the group consisting of H, —$C(CH_3)_2CN$, —$OCH_3$, —$S(O)_2CH_3$, CN, and —$C(CH_3)_2OH$;
or a pharmaceutically acceptable salt thereof.

2. A compound as claimed by claim 1 wherein the compound is:

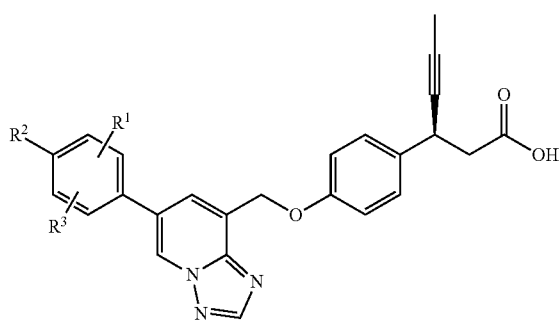

Wherein
$R^1$ is selected from the group consisting of H, $CH_3$, CN, —$CH_2CN$, —$C(CH_3)_2CN$, F, Cl, and Br;
$R^2$ is selected from the group consisting of H, —O($C_1$-$C_3$alkylene)$R^4$, —$CH_2CN$, CN, —$OCH_3$, $CF_2$, —$C(CH_3)_2CN$, —$C(CH_3)_2$, —$S(O)_2CH_3$, —$S(O)_2NH_2$, and —$OCF_2$;
$R^3$ is selected from the group consisting of H, $CH_3$, and —$OCH_3$; and
$R^4$ is selected from the group consisting of H, —$C(CH_3)_2CN$, —$OCH_3$, —$S(O)_2CH_3$, CN, and —$C(CH_3)_2OH$;
or a pharmaceutically acceptable salt thereof.

3. A compound, or pharmaceutically acceptable salt thereof, as claimed by claim 2 wherein $R^1$ is selected from the group consisting of H, $CH_3$, F, and Cl.

4. A compound, or pharmaceutically acceptable salt thereof, as claimed by claim 3 wherein $R^2$ is selected from the group consisting of H, —O($C_1$-$C_3$alkylene)$R^4$, —$OCH_3$, —$OCF_2$, and —$C(CH_3)_2$.

5. A compound, or a pharmaceutically acceptable salt thereof, as claimed by claim 4 wherein $R^3$ is selected from the group consisting of H and $CH_3$.

6. A compound, or a pharmaceutically acceptable salt thereof, as claimed by claim 5 wherein $R^4$ is selected from the group consisting of H, —$S(O)_2CH_3$, —$C(CH_3)_2OH$, and —$OCH_3$.

7. A compound, or pharmaceutically acceptable salt thereof, as claimed by claim 6 wherein $R^1$ is selected from the group consisting of H and $CH_3$.

8. A compound, or pharmaceutically acceptable salt thereof, as claimed by claim 7 wherein $R^2$ is selected from the group consisting of H, —O($C_1$-$C_3$alkylene)$R^4$, and $C(CH_3)_2$.

9. A compound, or pharmaceutically acceptable salt thereof, as claimed by claim 1 wherein $R^1$ is $CH_3$, $R^2$ is H, and $R^3$ is H.

10. A compound, or pharmaceutically acceptable salt thereof, as claimed by claim 9 that is (S)-3-[4-(6-o-Tolyl-[1,2,4]triazolo[1,5-a]pyridin-8-ylmethoxy)-phenyl]-hex-4-ynoic acid.

11. A pharmaceutical composition comprising a compound as claimed by claim 1, or a pharmaceutically acceptable salt thereof, and at least one pharmaceutically acceptable carrier, diluent, or excipient.

12. A method of treating type two diabetes in a patient, comprising administering to a patient in need thereof, an effective amount of a compound, or a pharmaceutically acceptable salt thereof as claimed by claim 1.

13. An intermediate compound which is

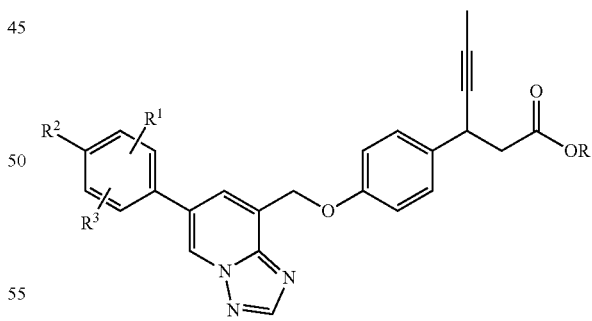

wherein
R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl;
$R^1$ is selected from the group consisting of H, $CH_3$, CN, —$CH_2CN$, —$C(CH_3)_2CN$, F, Cl, and Br;
$R^2$ is selected from the group consisting of H, —O($C_1$-$C_3$alkylene)$R^4$, —$CH_2CN$, CN, —$OCH_3$, $CF_2$, —$C(CH_3)_2CN$, —$C(CH_3)_2$, —$S(O)_2CH_3$, —$S(O)_2NH_2$, and —$OCF_2$;

$R^3$ is selected from the group consisting of H, $CH_3$, and $-OCH_3$; and
$R^4$ is selected from the group consisting of H, $-C(CH_3)_2CN$, $-OCH_3$, $-S(O)_2CH_3$, CN, and $-C(CH_3)_2OH$;
or a pharmaceutically acceptable salt thereof.

14. An intermediate compound as claimed by claim 13 wherein the compound is formula II

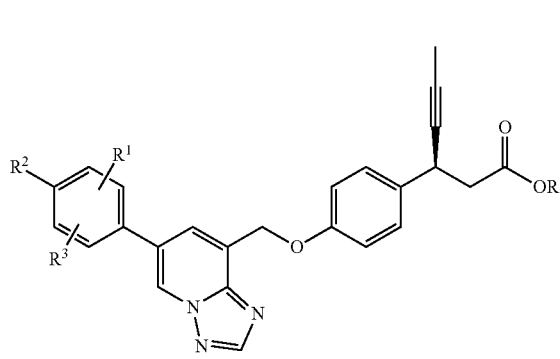

wherein
R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl;
$R^1$ is selected from the group consisting of H, $CH_3$, CN, $-CH_2CN$, $-C(CH_3)_2CN$, F, Cl, and Br;
$R^2$ is selected from the group consisting of H, $-O(C_1-C_3alkylene)R^4$, $-CH_2CN$, CN, $-OCH_3$, $CF_2$, $-C(CH_3)_2CN$, $-C(CH_3)_2$, $-S(O)_2CH_3$, $-S(O)_2NH_2$, and $-OCF_2$;
$R^3$ is selected from the group consisting of H, $CH_3$, and $-OCH_3$; and
$R^4$ is selected from the group consisting of H, $-C(CH_3)_2CN$, $-OCH_3$, $-S(O)_2CH_3$, CN, and $-C(CH_3)_2OH$;
or a pharmaceutically acceptable salt thereof.

15. An intermediate compound as claimed by claim 14, or a pharmaceutically acceptable salt thereof, wherein $R^1$ is $CH_3$, $R^2$ is H, and $R^3$ is H.

16. An intermediate compound or a pharmaceutically acceptable salt thereof as claimed by claim 15 wherein R is selected from the group consisting of methyl, ethyl, phenyl, and benzyl.

17. A method for preparing a compound as claimed by claim 2, said method comprising de-esterifying a compound of formula II;

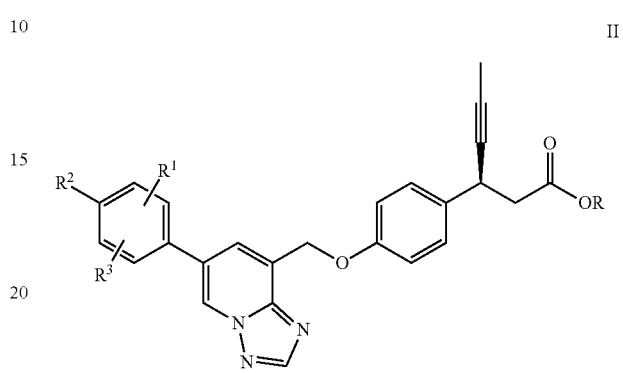

Wherein
$R^1$ is selected from the group consisting of H, $CH_3$, CN, $-CH_2CN$, $-C(CH_3)_2CN$, F, Cl, and Br;
$R^2$ is selected from the group consisting of H, $-O(C_1-C_3alkylene)R^4$, $-CH_2CN$, CN, $-OCH_3$, $CF_2$, $-C(CH_3)_2CN$, $-C(CH_3)_2$, $-S(O)_2CH_3$, $-S(O)_2NH_2$, and $-OCF_2$;
$R^3$ is selected from the group consisting of H, $CH_3$, and $-OCH_3$;
$R^4$ is selected from the group consisting of H, $-C(CH_3)_2CN$, $-OCH_3$, $-S(O)_2CH_3$, CN, and $-C(CH_3)_2OH$; and
R is selected from the group consisting of $C_{1-4}$ alkyl, $C_{1-4}$ haloalkyl, $C_{3-6}$ cycloalkyl, $C_{1-4}$ alkyl-$C_{3-6}$ cycloalkyl, phenyl, and $C_{1-5}$ alkylphenyl.

* * * * *

UNITED STATES PATENT AND TRADEMARK OFFICE
CERTIFICATE OF CORRECTION

PATENT NO. : 9,617,263 B2
APPLICATION NO. : 15/106998
DATED : June 21, 2016
INVENTOR(S) : Chafiq Hamdouchi et al.

It is certified that error appears in the above-identified patent and that said Letters Patent is hereby corrected as shown below:

On the Title Page

Column 2 (Abstract), Lines 4-5, delete "-O(C1-C$_3$alkylene)R4," and insert -- -O(C$_1$-C$_3$alkylene)R$^4$, --, therefor.

Column 2 (Abstract), Line 7, delete "CH3," and insert -- CH$_3$, --, therefor.

In the Claims

In Column 53, Line 62, in Claim 2, delete "Wherein" and insert -- wherein --, therefor.

In Column 54, Line 26, in Claim 8, delete "C(CH$_3$)$_2$." and insert -- -C(CH$_3$)$_2$. --, therefor.

In Column 56, Line 25, in Claim 17, delete "Wherein" and insert -- wherein --, therefor.

Signed and Sealed this
Twenty-ninth Day of May, 2018

Andrei Iancu
*Director of the United States Patent and Trademark Office*